United States Patent [19]

Mackey et al.

[11] Patent Number: 4,986,882

[45] Date of Patent: Jan. 22, 1991

[54] ABSORBENT PAPER COMPRISING POLYMER-MODIFIED FIBROUS PULPS AND WET-LAYING PROCESS FOR THE PRODUCTION THEREOF

[75] Inventors: Larry N. Mackey; Seyed E. Seyed-Rezai, both of Fairfield, Ohio

[73] Assignee: The Proctor & Gamble Company, Cincinnati, Ohio

[21] Appl. No.: 378,154

[22] Filed: Jul. 11, 1989

[51] Int. Cl.$^5$ .............................................. D21H 13/02
[52] U.S. Cl. .................................... 162/109; 162/111; 162/112; 162/113; 162/123; 162/146; 162/168.3; 162/182; 162/183; 162/184
[58] Field of Search ..................... 162/146, 111, 157.6, 162/112, 168.3, 148, 109, 113, 182, 183, 184, 149, 141

[56] References Cited

U.S. PATENT DOCUMENTS

| | | | |
|---|---|---|---|
| 3,256,372 | 6/1966 | Adams et al. | 264/28 |
| 3,589,364 | 6/1971 | Dean et al. | 128/284 |
| 3,793,299 | 2/1974 | Zimmerer | 260/17.4 |
| 3,889,678 | 6/1975 | Chatterjee et al. | 128/284 |
| 4,025,472 | 5/1977 | Lepoutre | 260/17.4 |
| 4,300,981 | 11/1981 | Carstens | 162/109 |
| 4,354,901 | 10/1982 | Kopolow | 162/158 |
| 4,552,618 | 11/1985 | Kopolow | 162/157.1 |
| 4,689,045 | 8/1987 | Armagnacq et al. | 604/375 |

*Primary Examiner*—Peter Chin
*Attorney, Agent, or Firm*—Lars S. Johnson; Jerry J. Yetter; Richard C. Witte

[57] ABSTRACT

Processes are described for making highly absorbent tissues and towels by wet-laying pulps comprising particular polycarboxylate polymer-modified fibrous pulps such as mildly hydrolyzed methyl acrylate-grafted softwood kraft pulps; these pulps have distinct protonated and alkali-metal-cation-exchanged states. The wet-laying processes are adapted to exploit the very different behavior of the polymer-modified fibrous pulps in function of the two states. The preferred wet-laying processes described herein are continuous processes embodying one or more on-line chemical treatment steps which chemically switch state of the polymer-modified fibrous pulp component in a wet web on the papermaking machine to improve the processing thereof by averting or minimizing tendencies to mechanically or thermally degrade.

20 Claims, 1 Drawing Sheet

ABSORBENT PAPER COMPRISING POLYMER-MODIFIED FIBROUS PULPS AND WET-LAYING PROCESS FOR THE PRODUCTION THEREOF

FIELD OF THE INVENTION

The present invention relates to the manufacture, by continuous wet-laying, of absorbent structures, especially absorbent paper webs which are useful in absorbent articles such as disposable paper towels, wipes and tissues. The processes disclosed include particular on-line chemical treatment steps.

BACKGROUND OF THE INVENTION

The notion of improving paper absorbent structures by incorporating therein a highly absorbent material is described in the art.

Amongst the disclosures which may be found, U.S. Pat. No. 4,252,761, Schoggen et al, issued Feb. 24, 1981, discloses that sheets may be prepared from certain modified fibrous carboxymethylcellulose derivatives, sometimes known as bibulous cellulosic fibers. Such sheets are described in patents including U.S. Pat. No. 3,678,031, Schoggen, issued July 18, 1972 and U.S. Pat. No. 3,589,364, Dean and Ferguson, issued June 29, 1971. Mixtures of these modified fibers with unmodified fibers are also disclosed in '761. The process of preparing the sheets comprises the steps of air-laying the fibers to form an airfelt, increasing the moisture content of the airfelt, and compacting the moisturized airfelt between a pair of opposed pressure-loaded rollers or between two planar members such as hydraulic rams.

Another approach, as taught in U.S. Pat. No. 4,295,987, Parks, issued Oct. 20, 1981, involves making a two-ply paper towel containing an air-laid, bonded, powdered particulate absorbent copolymer, the latter for example comprising acrylic acid, a crosslinking monomer, and a crosslinking agent. A layer of the particulate absorbent copolymer is sandwiched between two paper plies, each preformed according to the wet-laying process taught in U.S. Pat. No. 3,301,746, Sanford et al, issued Jan. 31, 1967. See '987, Example 2.

U.S. Pat. No. 4,076,663, Masuda et al, issued Feb. 28, 1978, disclose yet another highly water-absorbent material, having resinous form and prepared by polymerizing three components: a component chemically identified as starch or cellulose; a monomer having a polymerizable double bond which is water-soluble or becomes water-soluble by hydrolysis; and a crosslinking agent. The resulting product is then hydrolyzed if necessary. See Example 5, wherein the first component is "fluff pulp", the second component is a mixture of acrylic acid and sodium acrylate and the third component is N,N-methylenebisacrylamide. In this example, a ceric ammonium nitrate polymerization catalyst is also used. It is broadly stated that such resinous materials may be applied to absorbent articles, such as paper towels, by various methods including mixing the powdered resin with materials such as pulp, spraying an aqueous dispersion of the resin onto substrates such as pulp or paper, or immersing such substrates in aqueous dispersions of the resin followed by kneading and drying.

Brandt et al, U.S. Pat. No. 4,654,039, issued Mar. 31, 1987, reissued as U.S. Pat. No. Re 32,649 on Apr. 19, 1988, refer to a number of disclosures in the art of "hydrogel-forming materials which essentially comprise only cross-linked polymerized unsaturated monomers," in the sense that these materials have no starch or cellulose moieties. It is disclosed that water-extractable polymer material in such materials is undesirable. Improved "hydrogel-forming" materials, also of the non-cellulosic variety, having high gel volume, high gel strength, and low levels of extractable polymer, are the subject of the Brandt et al invention. These improved materials include a substantially water-insoluble, slightly cross-linked, partially neutralized, hydrogel-forming polyacrylate polymer. It is disclosed that various gross morphologies of the polymer, including fibers, can be used in an air-laid or laminated absorbent structure suitable for use in an absorbent article, the latter being defined as including, inter alia, diapers, paper towels and facial tissues.

Weisman, U.S. Pat. No. 4,610,678, issued Sept. 9, 1986, discloses flexible, substantially unbonded absorbent structures, especially useful for making thin diaper cores. These structures comprise what is described as a mixture of hydrophilic fibers and discrete particles of a water-insoluble hydrogel. Examples of the former include cellulose fibers and hydrophilized thermoplastic fibers; the latter are generally chemical compounds, including hydrolyzed acrylonitrile grafted starch as well as polyacrylates, which it is stated can be in fibrous form. The absorbent structures are generally prepared by dry processing, such as air-laying followed by compression. Weisman characterizes the notion of wet-laying mixtures of hydrogel particles and hydrophilic fibers as disadvantageous, in comparison with his invention. The specific disadvantages of wet-laying the hydrogel apparently include stiffness of the wet-laid product because of undesirable fiber-fiber bonding, as well as expense incurred by added drying load. Poor wicking characteristics of hydrogels and restricted swelling of hydrogel particles in a fibrous matrix are referred to as two possible causes for poorly performing hydrogel-containing webs.

Saotome, EP-A 192,216, published Aug. 27, 1986, describes another water-absorbent fibrous structure, characterized as comprising a fibrous cellulosic material impregnated with a waterabsorbent acrylic polymer and a fibrous material, which is produced by a method in which an aqueous solution of a monomeric component comprising acrylic acid and a radical initiator is diffused in a fibrous cellulosic material and heated, followed by blending with a fibrous material. It is stated that this material finds application in various absorbent articles, including disposable diapers and paper towels. There is not, apparently, any criticality in the kind of fibrous cellulosic material or fibrous material. The former may, for example, be a chemically purified wood pulp; the latter may be identical with the former or may comprise a synthetic fiber such as polyester. See Example 7, wherein acrylic acid, sodium hydroxide, N,N-methylenebisacrylamide and potassium persulfate are mixed and reacted in water, the resulting solution is sprayed over a chemically purified wood pulp, heated to obtain a polymerization product, and dried. This intermediate product is mixed with wood pulp, water and methanol and "vigorously stirred to bring the polymerization product to pieces." The mixture is wet-laid on a wire netting to make a sheet, and the sheet is dried.

Nakanishi et al, U.S. Pat. No. 4,721,647, issued Jan. 26, 1988, discloses absorbent articles comprising a base material of fibers, a part or all of which fibers are hydrophobic; and a water-absorbent polymer, a part or all of which is in the form of substantially spherical particles bonded to said fibers to surround them. Though little preparative detail is given, the article is apparently made by steps comprising spraying droplets of monomer onto the fibers, polymerizing such as by heat-curing, and drying.

In addition to the foregoing, there have been many other attempts to modify the properties of paper, both before the papermaking operation (such as by grafting fibers followed by wet-laying to form modified paper), as well as after the paper-making operation (such as by wet-laying fiber furnishes followed by grafting the paper). See, for example, "Chemical Modification of Papermaking Fibers," K. Ward, Jr., Marcel Dekker, N.Y., 1973. At page 171, Ward states: "Actual industrial utilization of grafting for paper has been minimal, although much time, money and effort have been spent in investigating the subject." At page 183, Ward states:"... grafting pulp with polymers which have a high affinity for water does not harm -and may even improve- the mechanical properties of paper made therefrom."

See also the more-recent disclosures of "The Chemistry and Technology of Cellulosic Copolymers," A. Hebeish and J. T. Guthrie, Springer-Verlag, New York, 1981. At page 336 it is stated: "There has been no evidence of the successful utilization of true grafting in the paper industry proper, although the Lenzing development of a fiber for nonwoven webs comes close to it." (In connection with the Lenzing material, see p335, paragraph 3 and cited).

See also U.S. Pat. No. 4,354,901, Kopolow, issued Oct. 19, 1982 and U.S. Pat. No. 4,552,618, Kopolow, issued Nov. 12, 1985. The Kopolow disclosures relate to compression or heat treatment of boards in the dry state after a wet-laying papermaking process. The boards comprise "hydrocolloidal fibers" such as those of U.S. Pat. No. 3,889,678, Chatterjee et al, issued June 17, 1975.

It is an object of the present invention to provide wet-laid absorbent paper structures in the form of paper webs which are capable of quickly absorbing and tenaciously retaining appreciable quantities of water and other aqueous fluids, yet are soft to the touch when dry and pleasant to handle even when wet, especially in not shedding particles of absorbent material or feeling unpleasantly "gel-like" when in use.

It is a further object to provide disposable absorbent articles having similar advantages, such articles including layered or homogeneous single-ply tissues, towels and wipes as directly made by the present process, as well as the products of conventionally converting the paper webs of the invention, e.g., by combining into a multi-ply article one or more plies of the absorbent paper structures of the invention. Such converted disposable absorbent articles include multi-ply tissues and towels or wipes.

In another mode, it is an object herein to apply the invention for the more economical provision of absorbent articles than was hitherto possible without sacrificing their water-absorbency, aesthetics or usefulness.

It is a further object of the invention to provide an improved continuous wet-laying papermaking process for producing the absorbent paper structures economically.

It is yet another object of the invention to provide processes for making particularly preferred polymer-modified fibrous pulps, as well as the products thereof such as a particularly made hydrolyzed, methyl acrylate grafted kraft pulp, being especially desirable as a fibrous pulp for use in admixture with conventional pulps in the absorbent paper structures of the invention.

BACKGROUND ART

Although the instant invention relates to a wet-laying process and to absorbent structures derived therefrom, two recent disclosures in the rather different fields of fiber-making and/or fiber-drying processes are of interest.

U.S. Pat. No. 4,025,472, Lepoutre, issued May 24, 1977, discloses a process for drying wet, highly swollen, polymer-modified cellulosic fibers to provide fibers having enhanced retention of both water and physiological liquids. The essential steps of the drying process are as follows: first, the hydrolyzed fibers are thoroughly washed with water, thus rendering them to a substantially maximum swollen state. The fibers are then acidified to a low, critical pH whereby the water previously retained by the alkaline fiber is released and filtered off, thus rendering them to a substantially minimum swollen state. Further treatment with an alkaline non-swelling solvent mixture renders the fibers substantially water-free in their alkaline salt form. A final wash and drying step using substantially water-free solvent and heat completes the process.

U.S. Pat. No. 4,689,045, Armagnacq, issued Aug. 25, 1987, discloses a dry fibrous product made from modified cellulose, assertedly having improved properties of absorption and water and physiological fluid retention, as well as a suitable production procedure. The cellulose contained in a cellulose paste is activated; acrylonitrile is grafted to the cellulose while its dry content is sufficient to obtain a grafting rate of about 200%; the grafted cellulose paste is hydrolyzed until a state of maximum expansion is reached; the product is acidified to a pH which brings it to a state of minimum expansion after which the water is removed; the product is converted to its salt form in the presence of a water-miscible liquid, and under agitation which is sufficient to prevent clustering of the fibers; this is effected so that the quantity of water, expressed by volume, does not exceed about 10% of the liquid phase; the product is finally dried.

Patents relating to papermaking processes generally useful in the context of the present invention and incorporated herein by reference include U.S. Pat. No. 3,301,746, Sanford et al, issued Jan. 31, 1967; U.S. Pat. No. 3,905,863, Ayers, issued Sept. 16, 1975; U.S. 3,974,025, Ayers, issued Aug. 10, 1976; U.S. Pat. No. 3,994,771, Morgan, Jr. et al, issued Nov. 30, 1976; U.S. Pat. No. 4,191,609, Trokhan, issued Mar. 4, 1980; U.S. Pat. No. 4,300,981, Carstens, issued Nov. 17, 1981; U.S. Pat. No. 4,440,597, Wells et al, issued Apr. 3, 1984; U.S. 4,469,735, Trokhan, issued Sept. 4, 1984; and U.S. Pat. No. 4,637,859, Trokhan, issued Jan. 20, 1987.

SUMMARY

The present invention relates to an improvement in a continuous wet-laying papermaking process for the manufacture of absorbent paper sheets from two or more fibrous pulps, wherein at least one of said fibrous pulps, A, is a polymer-modified fibrous pulp, as described more fully hereinafter, which, in its alkali-metal-cation exchanged state, imbibes water by hydrocolloidal swelling, and wherein the balance of said fibrous pulps, B, comprises conventional papermaking pulps, said process comprising the steps of web lay-down and dewatering.

The improved process herein comprises conducting the wet-laying process in the absence of interfering cationic materials, under conditions wherein pulp A is laid down in an embryonic web in a protonated state and wherein said embryonic web is at least partially dewatered, preferably to a consistency of about 15%, or higher, while maintaining pulp A in said protonated state.

Very preferably, pulp A is taken back from the protonated state to the alkali-metal-cation-exchanged state prior to final high-temperature drying of the web. Thus, in a preferred embodiment, the process comprises the sequence of steps: (a) treating a stock of said fibrous pulps A and B (they may be treated separately or in admixture) with acid; the amount of said acid being sufficient to ensure that in subsequent step (b), the type A component of said fibrous pulps is maintained in said protonated state; (b) wet-laying the acidic stock (A + B) formed in step (a) from a single-channel or multi-channel headbox onto a first foraminous member, thereby draining water to the extent of forming an embryonic web, said embryonic web having one or more layers; (c) at least partially dewatering the embryonic web in one or more steps to provide a partially dewatered web; (d) contacting the partially dewatered web of step (c) with alkali so as to bring the fibrous pulp type A component of the web to the alkali-metal-cation-exchanged state (preferably, the alkali-contacting means are comprised of a conventional spray-head); and (e) drying said web.

Due to the heat-sensitivity of the type A pulp which is capable of harming its absorbency, the process temperature throughout steps (a)–(e) preferably does not exceed about 200° C. Even more preferably, since the type A pulp is most heat-sensitive in the protonated state, temperatures are kept as low as practically possible before alkali-treatment step (d). To illustrate: when hot air predryers are used as part of the partial dewatering operation (c), the predryer inlet temperature is preferably set in the range from about 125° C. to about 175° C. Final drying step (e) is usually carried out using a conventional, commercial hot drum dryer, commonly known as a Yankee dryer, the temperature of which is preferably in the range from about 150° C. to about 175° C., most preferably from about 163°-170° C. which typically corresponds with a saturated steam pressure of 97-114 psi (669-786 kiloPascals).

The amount of acid in step (a) is generally such as to deliver a pH in the range of from about 3 to about 5, as determined in the water draining from said embryonic web. Preferably, the pH of water draining from the web in each of steps (b) and (c) is in the range from about 3.5 to about 4.5; pH at the end of step (d) is preferably in the range from about 6 to about 9, even more preferably 7-8. Water samples for pH measurement can be obtained by squeezing the web or, if the web is too dry, by equilibrating a sample of the web with pure water. The preferred consistency of the web at the end of step (c), i.e., immediately prior to alkali-treatment step (d), is in the range from about 15 % to about 75 %.

In general, fibrous pulp A comprises a covalently chemically bonded polymeric modifier consisting of a hydrophilic organic polycarboxylate polymer. Thus the preferred polymer-modified fibrous pulp (A) is a mildly hydrolyzed methyl acrylate grafted southern softwood kraft pulp, wherein the polymeric modifier is polyacrylate derived from the polymerization and subsequent hydrolysis of the methyl acrylate component; this polyacrylate is covalently chemically bonded to, as distinct from merely physically coating, the kraft pulp. The type B pulp is a conventional pulp, e.g., kraft pulp, sulfite pulp or chemithermomechanical pulp; such pulp is widely available in commerce; the type B pulp is not polymer-modified. Based on the total of pulps A and B, the proportion of pulp A is generally from about 1% to about 20%, more preferably from about 3% to about 15% and the balance of the pulp, to 100%, is pulp B. The acid used in the process is typically sulfuric acid, e.g., as an aqueous solution. The alkali is preferably a hydroxide, carbonate or bicarbonate of sodium or potassium; aqueous sodium carbonate is highly preferred on grounds of cost but potassium carbonate has superior solubility and has the advantage that it is more easily applied in concentrated aqueous form.

In general, the type A pulp has two states: a protonated state and an alkali-metal-cation-exchanged state. The invention embodies the discovery that the type A pulp responds differently to individual steps in wet-laying papermaking operations, depending on which of these states it is in: in the protonated state, pulp A is appreciably more resistant to disintegration during wet-laying and partial dewatering operations where mechanical shear forces tend to be high; whereas in the alkali-metal-cation-exchanged state, pulp A is more resistant to thermal degradation. Thus pulp A should invariably be in the protonated state at the wet-end of the papermaking operation, e.g., as laid down on a Fourdrinier wire. Very preferably, pulp A should furthermore be taken to the alkali-metal-cation exchanged state, as noted, prior to final high-temperature drying.

In practical terms, setting up "conditions wherein pulp A is laid down in an embryonic web in a protonated state" requires only that at the outset of the process, sufficient acid be brought into contact with pulp A. Due to the alkalinity reserves associated with the large volumes of process water used in wet-laying, and also to some extent due to the alkalinity reserves of the type B pulp, this amount of acid generally exceeds the theoretical amount for taking alkali-metal-cation-exchanged type A pulp to the protonated state. Thus, even when starting the process having a type A pulp in the protonated state, laying down pulp A in the protonated state requires the presence of a certain excess of acid. For best results, a suitable amount of acid is most conveniently specified on the basis that the pH of the recirculating process water (whether at the headbox, or draining from the embryonic web, or at the fan pump, or at the wire pit) is in the range from about 3 to about 5. Especially when starting up a continuous process, i.e., in situations where roughly steady-state acidic pH of the recirculating process water in the 3-5 pH range has not yet been achieved, it is highly preferred that the type A pulp should be brought to the protonated state before it reaches the fan pump (i.e., the point in the process at which it is customary to dilute papermaking pulps with large volumes of process water).

The present invention also requires that interfering cationic materials should not be present. Such materials interact adversely with the type A pulp, significantly affecting sheet formation by causing excessive pulp flocculation, as well as by reducing the absorbency benefits of the invention. Specific types and levels of interfering cationic materials, as well as general tests to determine if a particular cationic material is or is not interfering, are described at length hereinafter. Cationic wet-strength resins, such as KYMENE 557H (Hercules Inc.), are especially interfering, and under normal circumstances, their use in the process should be avoided.

In its product aspects, the invention encompasses absorbent paper structures, in the form of paper webs as directly produced by the instant process, as well as various absorbent articles which can readily be manufactured therefrom by conventional papermaking conversion operations. The product of the invention preferably takes the form of disposable tissues, towels and wipes.

Inter alia, the invention secures paper webs incorporating modest levels (e.g., 10%-20% based on total pulp) of water-absorbent or aqueous-fluid-absorbent type A pulps, yet having significantly greater absorbency than a conventional reference paper e.g., as illustrated by an equal basis weight wet-laid paper containing only type B pulp which is made by an entirely conventional wet-laying process.

In another mode, the invention encompasses highly economical q paper webs incorporating even lower levels (e.g., 3%-5% based on total pulp) of water-absorbent or aqueous-fluid-absorbent type A pulps. Even when such webs embody significant economies in terms of total usage of paper pulp (the content of type B pulp having been reduced by as much as 20% or more, thereby significantly reducing the basis weight), the webs have water or aqueous fluid absorbency which is fully equivalent to that of higher-basis-weight wet-laid reference paper. Higher-basis-weight reference paper can be made by an entirely conventional wet-laying process; as compared with the paper of the invention embodying a saving in the amount of type B pulp, no type B pulp has been removed; furthermore no type A pulp has been added.

Achieving such benefits is made possible by virtue of the fact that the present process does not materially harm the absorbency or absorbency rate of the type A pulp in the product paper web as compared with the absorbency or absorbency rate of the pulp A starting-material. As a result of these and other advantages, the invention is especially adapted for practical application in the manufacture of paper products such as disposable absorbent paper towels, where absorbent capacity coupled with economy and quick pick-up of spills are, for consumers, especially important product attributes. Unless otherwise noted, all percentages herein are by weight, temperatures are equipment operating temperatures, and the terminology relating to papermaking is conventional. The conventional terminology includes "stock", which refers to an aqueous suspension (usually relatively dilute) of papermaking fibers; and "consistency", which is the percentage by weight of fibrous material, dry basis, in any mixture containing water and papermaking fibers.

DETAILED DESCRIPTION OF THE INVENTION

Figure 1:
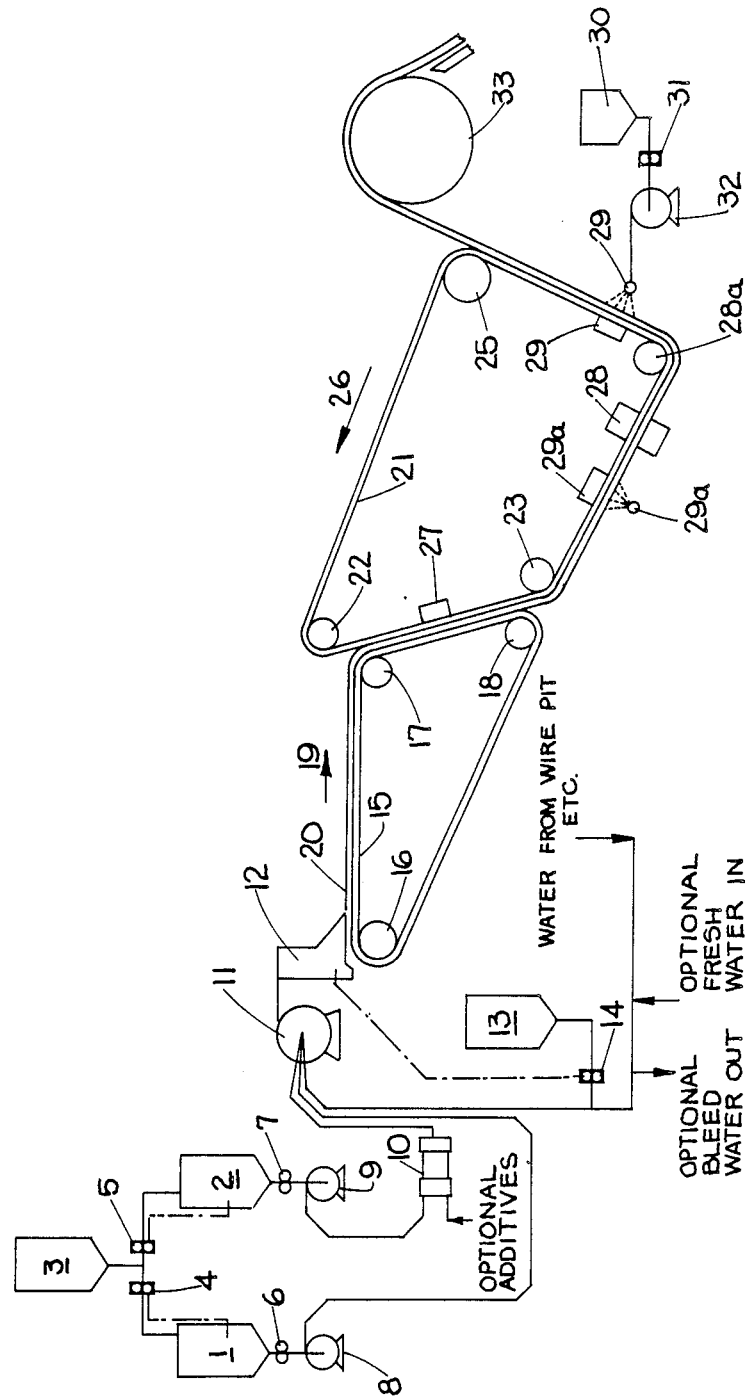
FIG. 1 is a schematic illustration of one embodiment of a continuous papermaking machine useful in the practice of the present invention.

The present invention relates to papermaking using continuous wet-laying papermaking equipment as distinct from relatively slow and more easily controlled batch processes such as handsheet making. "Continuous" papermaking processes in accordance with the invention operate at high speeds, e.g., about 500 ft/min (152.4 meters/min), or higher. Typical high speeds are from about 2,000 ft/min to about 4,000 ft/min (609.6 meters/min - 1219.2 meters/ min).

More specifically, the present invention relates to a process for wet-laying specific kinds of fibrous pulps to form paper webs suitable for use as disposable absorbents. The paper webs generally contain "fibrous pulps type A", which are particular, polymer-modified fibrous pulps; as well as "fibrous pulps type B", which are pulps of the kind conventionally used in disposable absorbent papers.

Fibrous pulps type A are potentially highly absorbent materials, but are difficult to incorporate into paper by wet-laying techniques. Significant processing problems are encountered and, ultimately, inferior product webs are made when the type A pulps are conventionally wet-laid. More specifically, these conventionally wet-laid webs tend to have an undesirable "hand", due to stiffness or wet "gel-feel", and furthermore tend to have significantly poorer absorbency than expected on the basis of having wet-laid into the paper web a supposedly highly absorbent fibrous pulp type A, usually at considerable expense.

The present invention overcomes these problems, and improves a wet-laying process so as to exploit fibrous pulp type A having two distinct states, namely a protonated state and an alkali-metal-cation-exchanged state. The process herein makes use of the different behavior of these two states of fibrous pulp type A under wet-laying papermaking conditions to provide the desired product, as follows:

FIG. 1 is a simplified, schematic representation of an embodiment of a continuous papermaking machine useful in the practice of the present invention.

Chests 1 and 2 are storage chests for aqueous dispersions of pulps of type A and type B, respectively.

Chest 1 contains an aqueous dispersion of type A pulp having a pH of from about 3.5 to about 4.5. The pH of the aqueous dispersion of type A pulp may be adjusted by adding aqueous sulfuric acid which is stored in storage vessel 3. The amount of acid added to chest 1 is controlled by metering device 4, incorporating pH sensing means situated in chest 1. The consistency of the aqueous dispersion of type A pulp may be adjusted by adding water. The type A pulp is most sensitive to water hardness whenever it is not in the protonated state; thus, when preparing the aqueous dispersion of type A pulp from type A pulp receipts which are in the alkali-metal cation-exchanged state, the water used to prepare and to adjust the consistency of the aqueous dispersion of type A pulp in chest 1 is typically deionized water, or soft water having a total water hardness (calcium plus magnesium) of 5 ppm or less. When preparing the aqueous dispersion of type A pulp from type A pulp receipts which are in the protonated state, the hardness of the water used to prepare and to adjust the consistency of the aqueous dispersion of type A pulp in chest 1 is less critical. Water having a total water hardness (calcium plus magnesium) up to about 150 ppm is then satisfactory.

Chest 2 contains an aqueous dispersion of type B pulp having a pH of from about 3.5 to about 4.5. The pH of the aqueous dispersion of type B pulp may be adjusted by adding aqueous sulfuric acid which is stored in storage vessel 3. The amount of acid added to chest 2 is controllable independently from the amount added to chest 1. Thus, the amount of acid added to chest 2 is controlled by metering device 5, incorporating pH sensing means situated in chest 2. The consistency of the aqueous dispersion of type B pulp may be adjusted by adding water. The water hardness of water used to prepare and to adjust the consistency of the aqueous dispersion of type B pulp in chest 2 is not as critical as the water hardness of water used or added in chest 1; typically, papermaking process water of good quality will suffice: such water has water hardness (parts per million, calcium plus magnesium) of from about 40 to about 150.

The aqueous dispersions of pulps A and B pass via valves 6 and 7 and pumps 8 and 9 to fan pump 11. Optionally, online mixer 10 can be used to add compatible additives, provided that such additives are non-interfering with respect to the type A pulp, as further discussed in detail hereinafter. At fan pump 11, the acidic stock is diluted by recycled process water. As shown in FIG. 1, the fan pump serves also to mix the type A and type B pulps. The diluted acidic stock, comprising pulps A and B, now passes to headbox 12, which can be of any convenient design. As process water is subsequently removed in the wet-end papermaking operation, it is collected from the wet-end using a water collection system comprising water collecting pans and a wire pit not shown, and recirculates via the fan pump to the headbox 12. The entire process water recirculation system is kept at an approximately constant pH in the range from about 3.5 to about 4.5 by adding aqueous sulfuric acid, as needed, using metering device 14 incorporating pH sensing means located at headbox 12. Optionally, additional process water bleed outlets, fresh process water inputs, and inline mixers may be provided, the better to control the process water composition. Having a separate acid storage Vessel 13 is not strictly necessary: if convenient, storage vessel 3 can be used to provide all the acid. However, whatever storage vessel delivers the aqueous sulfuric acid, metering devices 4, 5 and 14 each function independently so that acid may independently be added to the type A pulp, the type B pulp and the recirculating process water. In FIG. 1, broken lines are used to show the connection of metering devices to the aforementioned suitably positioned pH sensing means. Though less convenient than the continuous pH monitoring and acid adjustment shown, it is of course possible to monitor pH non-continuously by taking water samples at any stage in the process, measuring their pH, and adjusting the amount of acid accordingly.

From headbox 12, the acidic, diluted stock (now typically having a consistency in the range from about 0.15% to about 0.2%) is delivered to a first foraminous member 15, which is typically a Fourdrinier wire. Optional auxiliary units and devices commonly associated with stock preparation for papermaking machines but not shown in FIG. 1, may include refiners, as well as additional pumps, flow control and metering devices, stock storage chests and the like. The purpose of the stock preparation units and devices, illustrated and not illustrated, is to prepare acidic stock from pulps type A and type B, and further, to provide a uniformly pumped dispersion of papermaking fibers, in one or more streams, to the headbox.

In FIG. 1 as noted, the type A and type B pulps are shown as being mixed in fan pump 11 and as being laid down in a unitary nonlayered web by means of headbox 12. Alternate embodiments of the papermaking machine are equally practical. In one such alternate embodiment, headbox 12 is a multi-channel headbox and the fan-pump equipment 11 comprises two or more conventional fan pumps capable of separately pumping two or more pulp streams in parallel, and capable of diluting those separate streams with recycled process water without mixing the type A and type B pulp components. In such an embodiment, for example, a two-layered web can be laid down by passing two separate acidic stocks, one comprising the type A pulp (from chest 1) and the other, the type B pulp (from chest 2), in two separate streams, to a double fan-pump. The two separate streams, now diluted by recycled process water, pass to a conventional multi-channel headbox, and are laid down as a two-layer web. As the pulp is laid down, the pH is from about 3.5 to about 4.5 overall. In yet another alternate embodiment, a three-layered web can be laid down by passing three separate acidic stocks, one comprising the type A pulp (from chest 1) and each of the remaining two stocks comprising type B pulp (from chest 2) in three separate streams, to a triple fan-pump. The three separate streams, each now independently diluted by recycled process water, pass to a conventional multi-channel headbox, and are laid down as a three-layer web, wherein the type A pulp is "sandwiched" between two layers of the conventional, type B pulp. The pH of water draining from the web as it is laid down is again from about 3.5 to about 4.5.

First foraminous member 15 is supported by breast roll 16 and a plurality of return rolls of which only two, 17 and 18, are illustrated. The aforementioned breast roll 16 is typically a vacuum breast roll with internal shower. First foraminous member 15 is propelled in the direction indicated by directional arrow 19 by drive means not shown. Optional wet-end auxiliary units and devices commonly associated with papermaking machines, but not shown in FIG. 1, include forming boards, hydrofoils, vacuum boxes, tension rolls, support rolls, wire cleaning showers, and the like. The purpose of headbox 12, first foraminous member 15, and these auxiliary units and devices, illustrated and not illustrated, is to form an embryonic web of papermaking fibers; this particular assembly of equipment collectively being termed the "wet-end" of the papermaking machine.

After the aqueous dispersion of papermaking fibers is deposited onto first foraminous member 15, embryonic web 20 is formed by removal of a portion of the aqueous dispersing medium or process water, by techniques well known to those skilled in the art. Vacuum boxes, forming boards, hydrofoils and the like are useful in enhancing removal of this water. As indicated supra, a process water collection system collects and returns a major portion of the aqueous dispersing medium as it is removed from the embryonic web via first foraminous member 15; the recirculating process water or aqueous dispersing medium may contain varying levels of pulp not initially retained on the first foraminous member, and is recycled to the fan pump as indicated supra. Embryonic web 20 travels with first foraminous member 15 about return roll 17 and is brought into the proximity of a second foraminous member 21. Second foraminous member 21 is typically a second Fourdrinier wire, a woven transfer fabric of open-mesh construction, or a heat-resistant deflection member. Suitable transfer fabrics and deflection members are disclosed in detail in the hereinbefore-mentioned U.S. Patents.

Conventional means (not shown in FIG. 1) are generally used to assist transfer and pick-up of the embryonic web on the second foraminous member; such means can include, but are not limited to, conventional vacuum pickup shoes or the transfer head arrangement of U.S. Pat. No. 4,440,597, Wells et al, issued Apr. 3, 1984, which is incorporated herein by reference.

The second foraminous member is supported by a plurality of rolls of which 22, 23, 24 and pressure roll 25 are illustrated. Second foraminous member 21 is propelled in the direction indicated by directional arrow 26 by drive means not shown.

The purpose of this section of the papermaking machine is to continue dewatering of the embryonic web, thereby forming an intermediate (partially dewatered) web having a significantly lower water content. The dewatering operation in this section of the machine typically includes some mechanical dewatering. Mechanical dewatering can be carried out by applying differential fluid pressure, such as by means of vacuum box 27. This section also includes dewatering by predryer 28 which operates at carefully controlled temperatures, as discussed in more detail elsewhere herein. After further dewatering and predrying, the intermediate web, now preferably having a consistency of from about 50% to about 75%, arrives in contact with the second foraminous member at a spray and suction box arrangement 29. The spray is of conventional construction and is positioned so as to deposit aqueous alkali uniformly, substantially across the full cross-machine width occupied by the paper web; the suction box assists in drawing the alkali through the paper web. In an alternate effective arrangement, spray and suction box arrangement 29 can be re-positioned at 29a, that is to say, at a position before pre-dryer 28.

Alkali storage vessel 30, its associated delivery system comprising flow control device 31 and pump 32, are used in conjunction with the aforementioned fluid delivery spray 29 to apply aqueous alkali to the outwardly facing surface of the paper web.

The purpose of the spray arrangement is to treat the web with sufficient alkali to convert the type A pulp component to the alkali-metal-cation-exchanged state, in which it is most effective as a water-absorbing material. In terms of the process advantages associated with alkali treatment at this stage, the alkali treatment step improves the tolerance of the type A pulp for thermal drying.

The intermediate web continues motion indicated by motion arrow 26, and arrives at a conventional Yankee dryer arrangement 33, whereon the paper web is finally dried, taking care not to overheat. The Yankee drum temperature is generally not in excess of about 200° C., preferably 175° C. or less. The Yankee dryer can optionally include conventional adhesive applicator means, doctor blade, or other conventional creping means not shown in FIG. 1.

In another preferred embodiment of the invention, a stock is provided, wherein the pulp consists essentially of from about 3% to about 15% fibrous pulp type A, the balance of pulp (about 97% to about 85%) being fibrous pulp type B, dry basis. Conventional process water is present, subject to a limitation on the content of "cationic materials", which is discussed at length hereinafter. In this embodiment, fibrous pulp type A is a particular hydrolyzed methyl acrylate grafted southern softwood kraft pulp made by a particular process described in detail hereinafter, and fibrous pulp type B is a mixture of conventional hardwood kraft, softwood kraft and chemithermomechanical pulps. More generally, pulp B need not include chemithermomechanical pulp, but its use in the type B pulp leads to highly economical embodiments of the invention. Consistent with the content of cationic material being limited, the process water, e.g., as analyzed at the wire pit, may contain some water hardness, e.g., calcium and magnesium ions, but no deliberately added soluble multivalent metal cations, e.g., alum, or cationic synthetic wet-strength resins, e.g., KYMENE 557H (Hercules Inc.) are initially present or are added in subsequent process steps.

In this embodiment, the improved wet-laying process is carried out according to the following sequence of steps: (a) treating said stock with acid, aqueous sulfuric acid being highly preferred, so as to arrive at an acidic stock, the consistency of which is typical for wet-laying, e.g., in the range from about 0.05% to about 4%. The pH of the water in the pulp-acid-water mixture constituting this acidic stock is from about 3 to about 5, more preferably about 3.5 to about 4.5. This step is followed by (b) wet-laying said acidic stock from a conventional headbox onto a first foraminous member such as a Fourdrinier wire, thereby forming an embryonic web. Partial dewatering, (c), is now carried out as follows: (c-i) mechanically dewatering said embryonic web ("mechanical" dewatering, relying on the foraminous member and other conventional mechanical dewatering means such as table rolls and vacuum boxes is by definition partial); (c-ii) transferring the partially dewatered web using conventional means, such as a pick-up shoe, to a second foraminous member, such as an openweave fabric; and (c-iii) further mechanically dewatering said embryonic web thereon, preferably to a consistency in the range from about 15 % to about 25 %, typically using conventional mechanical and thermal dewatering means, the latter preferably in the form of a forced air predryer operating at an air temperature below about 200° C., more preferably in the range from about 125° C. to about 175° C.; thereby forming a partially dewatered web having a consistency in the range from about 50% to about 75%. The following step (d) involves contacting the partially dewatered web with alkali, in an amount sufficient to at least partially bring the fibrous pulp type A component to the alkali-metal-cation-exchanged state. More preferably, this step involves the use of enough alkali to substantially fully convert the type A pulp to the alkali-metal-cation-exchanged state. In general, such a condition is reached when the pH of the residual water in the alkali-contacted web is about 6 or higher. Typically, the alkali contacting step (d) relies on the use of a conventional spray, positioned so as to uniformly treat with alkali at least one of the two major surfaces of the web. The alkali-treatment step (d) is followed by (e) thermally drying, typically using a Yankee dryer, at controlled dryer temperatures, generally not in excess of about 200° C., more preferably, in the range from about 150° C. to about 175° C.

In the above-described embodiment, the specified equipment operating temperatures of the predryer and Yankee manifestly lie within the same ranges. This might suggest to those unfamiliar with papermaking that the paper web is no cooler in the predryer than on the Yankee dryer. In reality, papermakers will readily appreciate that this is not the case. The paper web has a significantly lower temperature in the predryer than on the Yankee. This is due to the relatively low web consistency and large amount of water being evaporated in the predryer, which carries away great amounts of heat, as compared with the Yankee where there is a relatively small heat loss due to the relatively smaller proportion of water being evaporated. Thus, what is actually being taught in this preferred embodiment of the invention is to carry out the alkali-contacting step prior to the high-heat final drying operation, while the web is as yet relatively cool.

In the above-illustrated preferred embodiment of the invention, which has both the acidification and the neutralization steps present in a particular sequence in the wet-laying papermaking operation, the alkali is generally an aqueous solution of an inorganic base, such as caustic soda or, more preferably, potassium carbonate or sodium carbonate.

Preferably, in step (d), care is taken not to add too much water along with the aqueous alkali, i.e., the alkali should not be overly dilute, or sheet control problems may develop on the high-speed papermaking machine. On the other hand, the use of overly concentrated alkali is also not preferred, since it may then be more difficult to pump and may tend to precipitate. In more detail, when using potassium carbonate, which as noted is a highly preferred alkali on solubility grounds, the concentration is typically about 4 Molar, or higher, more preferably from about 4 Molar to about 6 Molar. When using sodium hydroxide as the alkali, the concentration is preferably from about 4 Molar to about 8 Molar. Potassium hydroxide may be substituted for sodium hydroxide. Other alkalis which may be used herein, but are rather poorer in terms of solubility, are illustrated by potassium bicarbonate, sodium bicarbonate and sodium carbonate.

In the interest of optimizing sheet control and minimizing the drying load in the final drying stage, the preferred consistency of the partially dewatered web lies in the range from about 40% to about 75% as measured upon entry to the ultimate thermal drying step (e).

The acidification step (a) in the instant process ensures having fibrous pulp type A in the protonated state at stages in the process where mechanical shear forces would otherwise harm its integrity; invariably, the protonated state is maintained in the web-forming stage (b) as well as the partial web-dewatering stage, here illustrated by the sequence of steps (c) of the papermaking operation.

Without being bound by theory, individual pulp fiber integrity measurements indeed suggest that the fibrous pulp type A component better tolerates the shear forces encountered during the wetlaying process without undue loss of its structural integrity in the protonated state, as compared with the alkali-metal-cation-exchanged state. It is furthermore believed that having the fibrous pulp type A component in the protonated state results in an embryonic web which is more readily mechanically dewatered than an otherwise identically formed web in which the fibrous pulp type A component is in the alkali-metal-cation-exchanged state.

In the above, it is to be noted that the extent of acidification is not merely that which would be required to start the wet-laying process with fibrous pulp type A component temporarily in the protonated state; the protonated state needs to be maintained in the wet-end operations, at least until the embryonic web is partially dewatered as noted, since the natural alkalinity reserves of the process water and/or the fibrous pulp type B are otherwise capable of deleteriously reverting the type A pulp to the relatively fragile and difficultly dewatered alkali-metal-cation-exchanged state during wet-laying.

In practical terms, the type A pulps can usefully be manufactured at a facility remote from the papermaking plant, and can be acidified to convert them to the protonated state prior to shipping. This has the advantage of being able to ship at rather low water content, typically from about 10% to about 20% solids. In general, even when the type A pulp is shipped in the protonated state, it will still suffer from the above-identified reversion problem unless the practitioner further acidifies, to the extent necessary for the instant process. Thus, at the papermaking plant, more acid will generally still need to be added. Clearly, whether acidifying the type A pulp is done at the pulp manufacturing facility or inside the papermaking plant, or partially at each, is immaterial, since in either of these variations, an acidification step at the wet-end of the papermaking machine will (very preferably) be needed. Quite irrespective of the initial state of fibrous pulp type A, the total amount of acid used in the instant process is generally in excess of the total alkalinity given by the sum of the alkalinities of the type A and B pulps plus the papermaking process water. A satisfactory extent of acidification is conveniently measurable, given the knowledge that water draining from the foraminous member or members (e.g., the wire or drying fabrics) throughout steps (b) and (c) of the process should have a pH in the range from about 3 to about 5. Even more preferably, the pH of water draining from the web in each of steps (b) and (c) is in the range from about 3.5 to about 4.5 and the pH of a water sample, e.g., one extractable by squeezing a sample of the web, at the end of step (d) is in the range from about 6 to about 9, more preferably from 7 to about 8.

Also to be noted in relation to the acidifying step, if the fibrous pulp type A is initially in the protonated state, acidification of the pulp as a whole, to the necessary extent, may be accomplished quickly; there is no particularly critical time, and a few seconds' acidification time is generally sufficient. However, if fibrous pulp type A is not initially in the protonated state, sufficient acid contacting time, generally at least about 10 minutes, more preferably about 30 minutes to about 60 minutes, should be allowed to ensure that conversion to the protonated state occurs before the stock containing the type A pulp passes through the fan pump, where it is finally diluted and then passes to the headbox and wire. Clearly, such significantly long acidification times make it necessary, when the type A pulp receipts at the plant are in the alkali-metal-cation-exchanged state, to resort to acidifying the fibrous pulp type A in a stock chest having enough capacity to ensure that the continuous papermaking process will not be interrupted. Using such an arrangement, appreciable stock chest residence times, quite satisfactory for the present purposes, are common. The appearance of fibrous pulp type A may, if desired, be checked by microscopic examination. In the protonated state, discrete fibers of fibrous pulp type A are substantially unswollen, and at least on cursory examination, resemble conventional papermaking fibers to a much greater extent than in the alkali-metal-cation-exchanged state. In the latter state, discrete fibers of fibrous pulp type A are typically swollen to the extent of about 2.5 - fold to about 4-fold, or even more, relative to the protonated state thickness.

In relation to the the above-described preferred embodiment, the alkali-adding process step (d) deliberately places the fibrous pulp type A in the alkali-metal-cation-exchanged, highly absorbent state. This may appear surprising in view of the greater difficulty of drying fibrous pulp type A in that state. Without being bound by theory, fibrous pulps type A, especially particular chemical forms thereof discussed more fully hereinafter, tend to undergo chemical reactions adverse to the ultimate absorbency of the paper sheet if the heating of the web is not limited as indicated. Most importantly, discovery that such adverse elevated temperature chemical reactions are minimized in the alkali-metal-cation-exchanged state, as compared with the protonated state of the fibrous pulp type A, provides grounds for deliberately introducing the alkali-treatment step before the high temperature Yankee dryer in the above-described embodiment. the other hand, keeping the type A pulp in the protonated state through as many as possible of the early stages of the process assists dewatering and helps retain integrity of the fibrous pulp type A at the wet-end. It has already been explained supra that pre-drying prior to alkali treatment is quite acceptable, even if the predryer temperatures seem to suggest the web attains high temperatures similar to those used at the Yankee, in view of the reality of great evaporative cooling effects on the web in the predryer.

In another highly preferred embodiment, the above-outlined process can readily be adapted to lay down a layered web, for example by using a multi-channel headbox, and a web having two or three layers is laid down in a single or twin-wire former of conventional design. When three layers are laid down, pulp A is typically in the inner layer and pulp B is typically used to form two outer layers.

As noted, it is preferred to use a second foraminous member for later stages of mechanically dewatering the embryonic web. Very preferably, the second foraminous member takes the form of an open-weave fabric or, even more desirably, takes the form of a deflection member as described by Trokhan in the above-referenced U.S. Pat. No. 4,637,859.

Fibrous Pulps

Since numerous particulate materials, including "crumb-like" and regularly shaped hydrocolloid particles, have sometimes been referred to as "pulps" in the art, the term "fibrous pulp" is used herein to indicate that the pulps with which the instant invention is concerned, whether novel or conventional, generally have particle lengths and particle length-width (i.e., aspect) ratios typical of and suitable for wet-laying papermaking, and are not generally spherical or otherwise peculiarly shaped in any manner significantly detrimental to wet-laying.

Type A Pulp Materials

Although many materials variously characterized as "hydrogels", "super-absorbents", "absorbent polymers", "chemically modified cellulose", "polymer-modified pulp", etc. are known in the art, the terms "polymer-modified fibrous pulp", "fibrous pulp type A", or, for brevity, simply "type A pulp", used herein to refer to an essential starting-material, are more narrowly defined. Thus, the essential fibrous pulp type A herein can, in general, be considered as consisting essentially of a polymer-modified fibrous pulp having two distinct states: a protonated state, and an alkali-metal-cation-exchanged state. By definition, these states are associated with significant differences in chemical and physical properties. The terms used are not necessarily intended to insist upon absolutely complete substitution of all ion exchange sites by protons or alkali metal cations, respectively; only the extent of substitution which is practical is intended.

As characterized in the protonated state (whether wet or dry), the fibrous pulp type A generally has fibrous morphology. In the protonated state, the type A pulp fibers are relatively non-swollen and resemble, at least superficially, the unmodifed form of conventional fibrous pulp from which the type A pulps originally derive. In contrast, in the alkali-metal-cation-exchanged state, the fibrous pulp type A has the form of a substantially fibrous polyanionic hydrocolloid. For practical purposes the anionic charge is mostly polycarboxylate-derived. In preferred embodiments such as certain hydrolyzed grafted fibers, the mechanism of water absorption by the type A pulp fibers in the alkali-metal-cation-exchanged state is not necessarily strictly hydrocolloidal, the structure of individual fibers offering the additional possibility of capillary wicking. Invariably however, the type A pulp in the alkali-metal-cation-exchanged state is characterized by hydrocolloidal swelling upon wetting. Whether absorbing water entirely hydrocolloidally or with an additional contribution by some other mechanism, the total water or aqueous fluid absorbency of fibrous pulp type A is at least about 20 g/g, more preferably in the range from about 20 g/g to about 60 g/g, as measured by the Tea Bag Gel Volume (TBGV) method. Furthermore, the rate of water or aqueous fluid absorption of the type A pulp is rapid. Typically, the type A pulp is capable of absorbing water or aqueous fluids to the extent of reaching 90%, or higher, of the above-quantified total water or aqueous fluid absorbency, within 10 seconds or less. The rate can be measured by microscopy, e.g., a Video Enhanced Light Microscopy (VELM) method. Test methods are further discussed hereinafter.

As normally encountered in the alkali-metal-cation exchanged state, the polymer-modified fibrous pulp, i.e., fibrous pulp type A, is relatively fragile, tends to lose individual fiber structural integrity rather easily, and is difficult to dewater relative to conventional papermaking fibers on a wet-laying papermaking machine. In accordance with the invention, these problems are reduced to a useful extent, or even substantially overcome, when fibrous pulp type A is in the protonated state, as compared with the alkali-metal-cation-exchanged state wherein the fibrous pulp type A readily imbibes large quantities of water.

Both of the above-identified states of the fibrous pulps type A are heat-sensitive to a significantly greater degree than normal papermaking pulps, but for thermal stability at elevated temperatures, e.g., on the Yankee dryer, the alkali-metal-cation-exchanged state is greatly preferred.

The preferred type A pulps herein can be described as the product of a process of pulp-grafting followed by hydrolysis, provided that the grafting and hydrolysis processes involve forming a polymer having a hydrophilic polyanion (especially polycarboxylate) component effectively covalently bonded to a natural hardwood chemical pulp or natural softwood chemical pulp. The starting-material pulp to which the polymer is bonded is generally one having substantial natural fibrous integrity. In other terms, as noted, non-fibrous cellulosic particles, such as spherical particles, are not included in defining fibrous pulp type A; furthermore, particles made from cellulosics which have substantially lost their natural, layered character, such as those of rayon, are significantly less preferred than the naturally layered cellulosics, e.g., kraft pulps.

The preferred type A pulp, containing polymer chemically bonded to discrete pulp fibers, is further characterized in that after treating the starting pulp by grafting and hydrolysis, the degree of mercerization should remain relatively low. Control of mercerization conditions in the treatment of cellulosics under hydrolyzing conditions is generally known in the art, although its importance in the present context does not seem to have been appreciated. Thus, on one hand, several grafting and hydrolysis processes inherently acceptable for making fibrous pulps type A in terms of the degree of mercerization are known, as further illustrated hereinafter; on the other hand, an unsuitable grafting and hydrolysis process, in terms of the hydrolysis conditions being too extreme and the resulting degree of mercerization being excessive, is given in U.S. Pat. No. 3,793,299, Zimmerer, issued Feb. 19, 1974.

One especially preferred fibrous pulp type A for use herein is a hydrolyzed methyl acrylate-grafted kraft pulp produced by a process further described hereinafter.

This preferred fibrous pulp type A is illustrative of a kind of absorbent material having a superabsorbent element (a particular synthetic polycarboxylate polymer) covalently connected to a structural element (naturally derived cellulose fiber structure) which gives strength, integrity and processability in wet-laying relative to the lightly crosslinked polyacrylate absorbents of Brandt et al. discussed in background supra. Furthermore, whereas the Brandt et al polyacrylates require at least partial self-crosslinking to impart adequate water-insolubility for the intended use, self-crosslinking of polymer in the fibrous pulp type A is not essential, at least when fibrous pulp type A is a hydrolyzed grafted pulp. Without being bound by theory, wet-laying type A pulps in the manner of the instant invention is believed to significantly reduce or even eliminate certain disadvantages commonly associated with the use of chemically homogeneous crosslinked polyacrylate superabsorbents in tissues and towels, such as shedding of absorbent, gel blocking, film-forming, slow water wicking and gel feel. It should furthermore be noted that although the theoretical maximum absorbency of a Brandt et al type absorbent material may exceed the maximum absorbency of the type A pulp, the latter has an advantage in terms of quicker water or aqueous fluid pickup, i.e., rate.

In the preferred embodiments of fibrous pulps type A, the lignin content is relatively low. Over-processing, e.g., excessive mercerization, as well as excessive post-refining, sonication or the like, are all to be avoided to the extent practically possible. Over-processing is believed to undesirably increase pulp viscosity and/or fines levels, thereby impacting negatively on dewatering characteristics of the resulting pulp, or to produce too fine a structure in the remaining intact pulp fibers such that the water-accessible surfaces are closed and the water-absorbency (especially rate thereof) and structural integrity tend to be spoiled.

More generally, the preferred hydrolyzed grafted fibrous pulps type A can be characterized as the product of a grafting-and-hydrolysis process comprising: starting from a substrate pulp selected from the group consisting of kraft pulp and sulfite pulp, grafting said substrate pulp by reaction thereof in the presence of a polymerization initiator with one or more compatible monomers and hydrolyzing under mild conditions the intermediate fibrous graft copolymer so formed, thereby providing said polymer-modified pulp type A having said organic polycarboxylate polymer formed in-situ covalently bonded in or upon said substrate pulp.

In the above, it is especially preferred to graft said substrate pulp by reaction thereof in an aqueous medium in the presence of the polymerization initiator selected from the group consisting of a water-soluble salt of Ce(IV), Mn(III), or Fe(II) (as well-known in the art, Fe(II) is used with hydrogen peroxide copresent) and one or more of the compatible monomers selected from the group consisting of methyl acrylate, ethyl acrylate, acrylonitrile, acrylamide and mixtures thereof.

The most highly preferred polymerization initiator is Ce(IV) (especially as ceric ammonium nitrate), the most highly preferred compatible monomer is methyl acrylate and most preferably, the grafting reaction is carried out with said substrate pulp at a level of from about 20% to about 50%; said polymerization initiator is at a level of from about 0.5% to about 3% and said compatible monomer is at a level of from about 50% to about 80%. Very preferably, said polymerization initiator is the last-added component. The substrate pulp, polymerization initiator and compatible monomer are conveniently reacted together in said aqueous medium at low shear under an inert atmosphere at a temperature from about 10° C. to about 40° C., more preferably about 20° C. to about 40° C., for a period of from about 0.5 hours to about 10 hours.

The hydrolysis procedure is preferably as follows: any water used during the hydrolysis should be soft, i.e., substantially free from calcium and magnesium hardness. The intermediate fibrous graft copolymer, formed by the aforementioned reaction of substrate pulp, polymerization initiator and compatible monomer, is filtered to remove any unreacted compatible monomer, polymerization initiator, etc., as filtrate. Hydrolysis of the intermediate fibrous graft copolymer involves reaction with water and sodium hydroxide. In more detail, for a satisfactory hydrolysis which does not excessively mercerize the intermediate fibrous graft copolymer, the hydrolysis conditions are as follows: an initial aqueous concentration of intermediate fibrous graft copolymer in the range from about 1% to about 5%; an initial aqueous sodium hydroxide concentration in the range from about 1% to about 5%; a hydrolysis temperature in the range from about 8° C. to about 100° C., a hydrolysis time period in the range from about 0.5 hours to about 2 hours and an approximately atmospheric hydrolysis pressure. It is especially preferred to filter the hydrolyzed pulp at the end of the hydrolysis step and to use it directly as the type A pulp in step (a) of the wet-laying papermaking process without any intervening step of grinding, extruding, sonicating, or beating.

The fibrous pulps type A in the alkali-metal-cation exchanged state, in dry form, generally contain water-soluble cations, especially sodium, which can dissociate when the type A pulp-containing absorbent structure is exposed to water. The water-soluble cations balance the charge of the polymer anions (polyanions) chemically bonded to the pulp fibers in the type A pulp.

The fibrous pulps type A are generally chemically stable materials, the above-identified considerations of thermal stability and interaction with reactive cationic materials excepted. Apart from water-soluble alkali metal cations, which dissolve or dissociate, the fibrous pulps type A do not otherwise dissolve in water or aqueous fluids to any significant extent when in use.

Oxygen-polyanionic polymers, especially polycarboxylates, are typical of the synthetic polymers in fibrous pulp type A. Sulfur-or phosphorus-based polymer derivatives, such as found in phosphorylated pulps, are significantly less preferred; however at least partial substitution of sulfur- or phosphorus- based polymer derivatives for the oxygen analogs may be conceived of without departing from the spirit and scope of the invention. On the other hand, complete replacement of polycarboxylate by a polyanion having a significantly lower pKa is viewed as being unlikely to lead to a type A pulp which can successfully be processed by the instant wet-laying process.

Fibrous pulps type A can generally contain impurities, such as lignin, as alluded to supra. Catalyst residues and/or homopolymer of the water-absorbing component can also be present. However, homopolymer will in general not be present to the extent of introducing any significant amount of an undesirable water-extractable component as defined by Brandt et al.

Interfering Cationic Materials

It has been discovered that the wet-laying process of the invention should be carried out in the absence of interfering cationic materials. Interfering cationic materials generally encompass interfering polycationic polymers and interfering multivalent metal cations. The common water-soluble metal monocations such as those of sodium, potassium and lithium, in contrast, are non-interfering.

Interfering polycationic polymers are more specifically illustrated by the commonly known synthetic wet-strength resins of the cationic type, at levels customarily used for wet-strength generation. Examples include KYMENE 557H (Hercules Inc.), PAREZ 631NC (American Cyanamid), and polyethyleneimine. Of these materials, the most strongly interfering is KYMENE 557H.

Interfering multivalent metal cations are illustrated by trivalent metal cations in a water-soluble form, such as $Al^{3+}$, present in alums used at customary wet-laying papermaking levels. Provided that the acidic pH and order of steps specified for the process are followed, dissolved divalent metal cations, more specifically $Ca^{2+}$ and $Mg^{2+}$ at their normal levels in process water, are non-interfering, and are therefore tolerable herein. However if the type A pulps are exposed to water having high levels of these "water-hardness" cations prior to acidifying the type A pulp in accordance with the invention, they can irreversibly harm the absorbency of the type A pulp.

More generally, whether a cationic material is or is not interfering depends on both the type of cation and on the level. The following convenient test can be used to determine whether or not, over a range of conventional levels of use for wet-strength additives, retention aids etc., in wet-laying (e.g., 0.001%-2%), any given cationic material is "interfering" and is therefore unacceptable herein.

In outline, the test involves determining whether any particular level of the cationic material flocculates an aqueous test suspension containing a mixture of type A and type B pulps as used in the instant process. In one suitable test, the pulp consists of 0.01% type A pulp, dry basis, and 0.09% type B pulp, dry basis. The pH of the aqueous test suspension is in the same range as that used in the process; in one embodiment of a suitable test, the pH is in the range 3.5–4.5. If flocculation occurs when the cationic material is added to the aqueous test suspension, the cationic material is considered as interfering: its use should be avoided in the instant process. A second convenient test is used to determine whether a cationic material is interfering on the basis of having a damaging effect on the absorbency of the type A pulp. A series of samples of type A pulp, typically about 1 gram in weight, in water (pH 3.5–4.5, consistency about 0.1%) are treated with the cationic material, the ratios of weights of the type A pulp to the cationic material in the series of samples encompassing a range of from about 10:1 to about 100:1. The samples are filtered to drain free water and are heated in an oven at about 100° C. to about 105° C. for about 1 hour. The absorbency of the dried treated pulp samples is determined using the TBGV test described hereinafter. If the absorbency and absorbency rate of the treated type A pulp are now found to fall outside an acceptable range for a type A pulp as specified elsewhere herein, the cationic material is interfering: its use should be avoided in the instant process.

The above-described tests are successful in identifying numerous interfering cationic materials which flocculate the mixture of type A and type B pulps, especially when added at the wet-end, or which irreversibly harm the absorbency of the type A pulp component.

It will be clear from the foregoing that whether a given cationic material is interfering depends to a great extent on whether it dissolves, to a type A pulp-reactive form, in the process water: if it does, e.g., $Al^{3+}$ in alum, it is interfering; if it does not dissolve, e.g., $Al^{3+}$ in sodium aluminosilicate, it is non-interfering.

Whether a given cationic material is interfering also depends on whether it is acid-reactive or acid-unreactive. Acid-reactive cationic materials are generally interfering, at any stage of the instant process where the process water is acidic. However, after treating the paper webs herein with alkali so as to neutralize them, an otherwise acid-reactive water-insoluble cation-containing material can be added to the web, and the cation therein is non-interfering.

Adventitious metal cations, especially divalent cations such as those of calcium and magnesium, at levels acceptable in conventional wet-laying process water, are tolerable, subject to the above-noted provision of not exposing the type A pulp to large amounts thereof prior to the acidification step in the instant process. In practice this will generally mean that if the water recycling in the process from the wet-end through the fan pump tends to have high "hardness", the type A Pulp is best acidified prior to reaching the fan pump, where considerable stock dilution occurs and an incompletely acidified type A pulp would therefore be most vulnerable to the hardness cations. Clearly, the above-identified tests can be used to check whether the process water has unacceptably high hardness. Very preferably, the levels of such adventitious metal cations in solution in the process water as "hardness" can be minimized by conventional water-treatment techniques. Moreover, deliberate dissolution of multivalent metal cations in the process water is generally to be avoided: this exclusionary measure is the same as is practiced for interfering cationic polymers. In short, switching fibrous pulp type A to the protonated state in the manner of the instant process is accompanied by a significant relative decrease in fragility and increase in ease of dewatering as compared with the alkali-metal cation exchanged state, and furthermore brings about a significantly improved tolerance for hard water in the process; but interfering cationic materials, especially objectionable cationic polymers as illustrated above, need to be excluded quite regardless of the state of the type A pulp.

Type B Pulps and Other Materials Used in the Process

The preceding discussion has emphasized the relatively unusual fibrous pulp type A component used in the instant wet-laying papermaking process. Fibrous pulp type B is conventional wet-layable fibrous pulp compatible with the type A pulps. More specifically, fibrous pulp type B is illustrated by a variety of conventional pulps such as kraft pulps of hardwood or softwood, chemithermomechanical pulps and sulfite pulps. Typical type B pulp is further illustrated by northern softwood kraft pulp, southern softwood kraft pulp, a mixture consisting essentially of northern softwood kraft pulp and eucalyptus pulp, and a mixture consisting essentially of northern softwood kraft pulp and chemithermomechanical pulp. When the type B pulp is a mixture, the relative proportions of the constituent conventional pulps may vary widely. Depending on the intended use of the paper structure, recycled pulps may also be used as type B pulp in the instant process. Preferred mixtures of conventional fibrous pulps used as the type B pulp component are illustrated by a type B pulp blend consisting essentially of 60% kraft pulp and 40% eucalyptus pulp; and another, consisting essentially of 70% kraft pulp and 30% chemithermomechanical pulp, dry basis.

The type B pulp can be used in admixture with the type A pulp at various levels. Preferably, the relative proportions of type A and type B pulps, together constituting the total pulp used herein, are such that the total pulp, dry basis, consists essentially of from about 1% to about 20%, more preferably about 3% to about 15%, most preferably 5% to about 15% fibrous pulp type A and from about 80% to about 99%, more preferably about 85% to about 97%, most preferably 85% to about 95% fibrous pulp type B.

As noted, the acid most suitable for use in the instant wet-laying process is sulfuric acid. Sulfuric acid is inexpensive and papermaking equipment is more tolerant of this acid than other relatively inexpensive acids, such as hydrochloric acid. Alkalis suitable for use herein include sodium hydroxide, sodium bicarbonate, sodium carbonate, potassium hydroxide, potassium bicarbonate and potassium carbonate. Preferably, the alkali is in the form of an aqueous solution, typically having high concentration, e.g., the maximum concentration consistent with the solubility of the alkali in water. Potassium carbonate is particularly preferred.

Optionally, various compatible chemically homogeneous carboxymethylcelluloses, powdered absorbent copolymers, resinous polymers, starch acrylates, etc., such as those referred to in background hereinabove, can also be used in the instant wet-laying process, provided that they are nonionic or anionic in character. No such materials, it will be clear, are included in defining the essential polymer-modified pulp (the type A pulp). Preferably, these particular optional materials will be avoided altogether.

Additional Embodiments of the Process, also Incorporating Optional Compatible Wet-Strength Additives Although the present process is generally practiced in the absence of cationic wet-strength resins such as KYMENE, which harm the absorbency of the type A pulp, certain compatible wet-strength additives can be used herein. Such compatible wet-strength additives are generally nonionic or anionic, rather than cationic in character. Examples of compatible wet-strength additives are provided by the anionic or nonionic (but not the cationic) watersoluble ionic-hydrophilic vinylamide polymers of U.S. Pat. No. 3,556,932, Coscia and Williams, issued Jan. 19, 1971, incorporated herein by reference. It is emphasized that the cationic polymers identified in '932 are unsuitable for use herein, i.e., they are considered interfering cationic materials for purposes of the present process. Preferred compatible wet-strength additives are the glyoxylated anionic polyacrylamides of '932. More specifically, these preferred compatible wet-strength additives are illustrated by Examples 6, 7 and 9 of '932; the wet-strength additive of '932 Example 6 is especially preferred.

Use of a compatible wet-strength additive in accordance with the present invention differs specifically from '932 in that co-use of alum with the compatible wet-strength additive is not permitted since, as taught hereinabove, the alum is incompatible with the type A pulp.

The compatible wet-strength additives do not act as interfering materials, i.e., they do not harm the absorbency of the type A pulp. Furthermore, their crosslinking to generate wet-strength in the web very preferably occurs at temperatures which are significantly below those temperatures identified hereinabove as being capable of harming the absorbency of the type A pulp.

Preferred embodiments of the wet-laying process of the invention giving stronger webs than those more generally obtainable, involve an additional, wet-strength-adding step, comprising spray-on to the web, by means of a conventional spray-head, of the above-identified compatible wet-strength additives, said additional, wet-strength-adding step intervening at any stage of said process between step (b) and step (e). Even more preferably, said additional, wet-strength-adding step is positioned immediately after step (d) and immediately prior to step (e).

Product Webs

The most commonly prepared absorbent structures in accordance with the invention will contain fibrous pulp type A in the alkali-metal-cation exchanged state, since the artisan will most likely practice not only the essential acidification step, but also the optional but highly preferred alkali-treatment step of the instant process. The corresponding absorbent structures contain fibrous pulp type A in the highly absorbent, alkali-metal cation-exchanged state, and the absorbent structure can directly be used as an absorbent article (e.g., a single-ply paper towel or wipe). Naturally, it is also possible to make more complex absorbent articles, for example multi-ply towels wherein at least one ply is in accordance with the invention.

Naturally, if the practitioner is prepared to forego the advantages associated with the alkali-treatment step in the instant process, the acidic mixture of fibrous pulps type A and B can be used in accordance with the invention to make an "acidic" ply, which can be sandwiched between alkaline plies made from conventional pulp so as to secure particular multi-ply absorbent articles. When spills are wiped using this type of absorbent structure, the alkali is liberated and converts the type A pulp to the highly absorbent alkali-metal-cation exchanged state, in-situ.

More generally, the paper webs formed by the instant process are absorbent structures, more specifically sheets, which can be used in numerous forms of absorbent article where quick absorption and good water-absorbing capacity and retention of water or other aqueous fluids is required, all without encountering significant aesthetic disadvantages such as "gel-feel" when the absorbent article is wet, or stiffness or absorbent material "shedding" when it is dry. The paper sheets of the invention are directly useful as single-ply tissues or towels, or are indirectly useful as an element of multi-ply disposable paper tissues, towels and wipes; or are further indirectly useful through conventional papermaking converting operations yielding catamenial articles and dressings of various kinds.

In addition to the process described in detail hereinabove, the invention encompasses a preferred embodiment of an absorbent structure, in the form of a wet-laid paper sheet, having the following characteristics:

The absorbent structure comprises from about 5% to about 15% of fibrous pulp type A. The pulp type A consists essentially of a polymer-modified fibrous pulp having distinct protonated and alkali-metal-cation-exchanged states. As characterized in the protonated state, pulp type A has relatively non-swollen fibrous morphology. As characterized in the alkali-metal-cation-exchanged state, pulp type A has the form of a substantially fibrous polyanionic hydrocolloid further characterized by hydrocolloidal swelling upon wetting, to the extent that said fibrous pulp type A has a water or aqueous fluid absorbency of from about 20 g/g to about 60 g/g, measured by the TBGV method, and a rate of water or aqueous fluid absorption such that said fibrous pulp type A reaches at least 90% of its maximum water-absorbing capacity within 10 seconds, measured by the VELM method. The polymer-modified fibrous pulp (pulp type A) is characteristically fragile and difficult to dewater in the wet, alkali-metal-cation-exchanged state as compared with conventional papermaking fibers and is furthermore susceptible to deactivation as an absorbent upon exposure to either of both of the classes of cationic materials (i) multivalent metal ions such as are commonly present in papermaking process water and (ii) cationic polymers or cationic polyelectrolytes conventionally known for use in papermaking for improving paper wet-strength. Polymer-modified fibrous pulp type A is also characterized by a significant relative decrease in fragility, increase in ease of dewatering and increase in resistance to multivalent metal ions in the protonated state as compared with said alkali-metal-cation-exchanged state.

The balance (to 100%) of the absorbent structure comprises conventional papermaking pulp (type B pulp) and, optionally, non-interfering additives, such as the glyoxylated anionic or nonionic (but not cationic) polyacrylamides described in U.S. Pat. No. 3,556,932.

The properties of the absorbent structure, i.e., the paper sheet, are as follows: density in the range from about 0.05 g/cm$^3$ to about 0.25 g/cm$^3$; mean water or aqueous fluid absorbency of the sheet in the range from about 2 g/g to about 10 g/g as measured by the TBGV method; and total wet tensile, machine direction plus cross-machine directions, in the range from about 500 g/inch (197 g/cm) to about 1500 g/inch (591 g/cm). Furthermore, the paper is the product of a process comprising both wet-laying said pulps and at least partially dewatering the resulting wet paper sheet whilst maintaining fibrous pulp type A in the protonated state; said wet-laying and partial dewatering operations being conducted in the substantial absence of interfering cationic materials.

EXAMPLES

The following examples illustrate particularly preferred type A fibrous pulps, and further illustrate the papermaking process of the invention. When any measurement is represented by two values, the units corresponding with the first value given are those of the experimental measurement (these units are commonly used by papermakers in the United States of America). The units of the second value, when present, are Metric System units, and are based on applying metric conversion factors to the first value. Unless otherwise indicated, the paper properties are reported for a single ply of paper, i.e., as directly produced using the machine illustrated in FIG. 1 hereinabove.

EXAMPLE 1

Preparation of Polymer-Modified Pulp Fibers, fibrous pulp type A, by grafting and hydrolysis process Starting-Materials Conventional kraft pulp fibers are used as the substrate pulp; more specifically, southern softwood kraft (SSK), HP-11 grade, Foley Plant, from Procter and Gamble Cellulose, Buckeye, is quite suitable. Methyl Acrylate, used to polymer-modify the SSK pulp, is obtained from Polyscience Inc. or Pfaltz & Bauer Inc. Ceric Ammonium Nitrate (anhydrous, crystals) is obtained from Fisher Scientific Co.

The equipment comprises a grafting reactor, which is a conventional stainless steel stirred reactor of about 125 gallon (about 473 liter) capacity equipped with steam-heating coils. Also used is a centrifuge (Buck, Model 755, 30 inch (76.3 cm) diameter bowl, 5 horsepower (3.73 kW), 1725 rpm.) The same reactor is used for both the grafting step and the hydrolysis step.

The grafting of the substrate pulp is carried out as follows: Weigh out 3.5 kg bone dry HP-11 (SSK, Southern Softwood Kraft). Soak the HP-11 pulp fibers in about 110 gallons (about 416 liters) water overnight. Tap water can be used, but the water is more preferably demineralized. After overnight soak, add about 280 ml of concentrated nitric acid, mixing effectively but not at high shear; pass nitrogen gas into the resulting mixture, thereby purging air dissolved in the mixture. Continue light mixing and passage of nitrogen for about 30 minutes; a pH reading taken at this stage should preferably yield a pH value in the range from about 2.0 to about 2.5. Add 10.5 liters of methyl acrylate to the mixture and stir for about 20 minutes. Add 241 g of ceric ammonium nitrate dissolved in 2 liters of water. Mix for about 5 minutes. (An increase in mixing speed will generally be required at this stage to ensure good dispersion of ceric ammonium nitrate.) Stop mixing and passage of nitrogen. Allow the mixture to stand for about 4 hours, during which time the methyl acrylate-grafting reaction occurs. Pump the mixture into a centrifuge and wash with about 220 gallons (833 liters) demineralized water, using a centrifuge speed of about 1725 rpm to separate the wash water from the methyl acrylate-grafted pulp. Typically, about 12 kg of methyl acrylate grafted pulp (dry basis) is obtained. (This pulp illustrates pulp of the general type referred to elsewhere herein as "intermediate fibrous graft copolymer").

Hydrolysis of the methyl acrylate grafted pulp is carried out under mild conditions, as follows: Transfer the methyl acrylate-grafted pulp into the clean hydrolysis reactor Add an amount of water calculated to give a mixture containing 2.5% solids and 97.5% water upon completion of the hydroxide addition step infra. Mix slowly and thoroughly. Add sodium hydroxide (fresh 50% aqueous solution) in an amount of about 0.82 liters/kg of methyl acrylate grafted pulp. Typically, about 10 liters of sodium hydroxide solution are required when operating at the scale of the instant example. Heat the mixture to about 90° C. by passing steam through coils in the reactor. Stop mixing. Let hydrolysis reaction proceed for about 2 hours. Pump the hydrolyzed methyl acrylate-grafted pulp mixture to a centrifuge.

Acid treatment and washing is now carried out as follows: Centrifuge the mixture to remove as much of the sodium hydroxide as possible. With the centrifuge running, pump in an acid solution (made from about 5 liters sulfuric acid (99%) in about 130 gallons (492 liters) of demineralized water), treating the hydrolyzed, methyl acrylate-grafted pulp with this acid solution until the pH of the effluent from the centrifuge drops to about 2.0. Carry out a follow-up washing with a second, more-dilute, acid solution (316 ml concentrated sulfuric acid in about 300 gallons (about 1135 liters) of demineralized water) After follow-up washing, centrifuge (1725 rpm) for about 15 minutes and remove the polymer-modified type A pulp fibers. Use these fibers without further treatment as type A pulp in the Examples hereinafter. The absorbency (TBGV method) of the product type A pulp in the alkali-metal-cation-exchanged state is about 40 g/g (pH 8); in the protonated state, the absorbency (TBGV method) is about 4 g/g (pH 2).

EXAMPLE 2

A paper sheet is produced in accordance with the process illustrated and described in connection with FIG. 1.

Fibrous pulp type A is the product of Example 1. Fibrous pulp type B is a mixture of chemithermomechanical pulp (Quesnel Co.) and bleached northern softwood kraft pulp (Grand Prairie, P&G Cellulose). The type A pulp is made up into a stock having a consistency of about 0.6% in chest 1 using water having a hardness of less than 5 ppm (calcium plus magnesium). Process water supplies used at other stages of the papermaking operation have hardness of about 100 ppm (calcium plus magnesium). No cationic materials, whether in the form of cationic wet-strength resins or aqueous polyvalent metal cations, are added at any stage. Aqueous concentrated sulfuric acid is in storage vessel 3; (corrosion-resistant steels are generally used in the constructing of all process equipment herein which may be exposed to corrosive acids). The aqueous dispersion of type A pulp in chest 1 has a pH of about 3.5. The pH of the aqueous dispersion of type B pulp in chest 2 is about 3.5 and the consistency is about 3%. The headbox 12 is a Fixed Roof Former, equipped with (a) a multi-orifice distribution plate to redirect incoming furnish and distribute it equally over the width of the first foraminous member, (b) a chamber to promote turbulence in the distributed flow and to prevent flocking, (c) a flow channel to carry the furnish to the first foraminous member and (d) distribution leaves to further promote turbulence. The consistency of the acidic stock at the headbox is about 0.15-0.2%. First foraminous member 15 is 84-mesh, 5-shed, M-design, with filament diameter of 0.17 inch (4.3 millimeters) in the warp and shute, specifically, 84-M DURAFORM Pilot Machine Fabric, obtainable from Albany International Corp., Appleton Wire Division. This foraminous member moves continuously at 500 feet per minute (about 152.4 meters per minute). Flow and wire movement are regulated so that a uniform, moist web (embryonic web) is laid down. The pH of water draining from this embryonic web is about 3.7. The embryonic web travels as shown in FIG. 1 until it is transferred by means of a conventional vacuum pickup shoe (not shown in FIG. 1). The location of the vacuum pickup shoe is conventional, i.e., between 22 and 27 and it is positioned so as to assist transfer of web 20 from first foraminous member 15 to second foraminous member 21. The vacuum pickup shoe operates at a vacuum of 8-9 inches of mercury (27.04-30.42 kiloPascal). Second foraminous member 21 is a woven synthetic transfer fabric, 1M×25, 3S, obtainable from Appleton Wire Division of Albany International Corp.

The paper web 21 arrives at a spray-and-vacuum box at the alternate position 29a and is there treated with aqueous potassium carbonate having a concentration of about 4 M (mole per liter) by means of a VIB sprayer, VIB Systems Inc., nozzle size 1 mm, 4 nozzles spaced over 16 inches (40.64 cm), air atomization. The alkali passes into the web, and there in-situ, takes type A pulp from the acidic state to the alkali-metal-cation-exchanged state. Some water and unreacted alkali are removed from the web by the spray-and-vacuum box 29a by applying a vacuum typical for tissue-paper making, e.g., about 8-9 inches of mercury (27.04-30.42 kiloPascal). The web now has a consistency of about 20.7% and enters a conventional forced air predryer 28. This predryer is (in common with all the other parts of the paper machine which handle the wet paper web) so designed as to avoid compacting the web: instead, drying is here achieved by passing hot air through the moist paper web and through the second foraminous member. The predryer air inlet temperature is about 175° C. The paper web has a consistency of about 50% on the second foraminous member leaving the predryer. The web continues motion indicated by motion arrow 26, and arrives at a conventional Yankee dryer arrangement 33, whereon the paper web is finally dried. The Yankee dryer includes conventional adhesive applicator means and a doctor blade for creping. The Yankee operates at a temperature of about 168° C. A conventional polyvinyl alcohol glue (0.025% solution) is conventionally applied to bond the web to the dryer drum, and 15% creping is applied. If desired, some calendaring and further converting operations may be carried out, e.g., to make two-ply towels. The properties of the resulting paper sheet are as follows:

| | |
|---|---|
| Process pH prior to alkali treatment | 3.5 |
| pH of paper | 7.5 |
| Pulp composition (% as laid down) | |
| Type A | 15.0 |
| Type B CTMP* | 25.0 |
| NSK** | 60.0 |

-continued

| Creped Basis Weight | |
|---|---|
| (lb/3000 sq. ft) | 16.5 |
| (g/sq. meter) | 26.9 |
| Absorbency of type A pulp (TBGV, g/g at pH 7-8) | 37.0 |
| Absorbency of paper (TBGV, g/g) | 8.6 |
| Absorbency Rate of paper (sec) | less than 10.0 |
| Spill Wipe Up, measured as two plies | significantly better than control (Example 7) or commercial BOUNTY towel |
| Integrity of type A pulp in paper (VELM) | good |
| Caliper under load of 95 g/5 cm dia | |
| (mils) | 11.2 |
| (millimeter) | 0.284 |
| Density (g/cm$^3$) | 0.090 |
| Dry Tensile Strain (%) | |
| Machine Direction | 19.9 |
| Cross Machine Direction | 5.3 |
| Dry Tensile Force: 4 inch (10.16 cm) gauge length | |
| Machine Direction (g/in) | 610 |
| (g/cm) | 240 |
| Cross Machine Direction (g/in) | 528 |
| (g/cm) | 208 |
| Wet Tensile Force: 4 inch (10.16 cm) gauge length | |
| Machine Direction (g/in) | 12 |
| (g/cm) | 4.7 |
| Cross Machine Direction (g/in) | 8 |
| (g/cm) | 3.2 |

*CTMP = chemithermomechanical pulp as described in Example 2, dry basis
**NSK = Northern Softwood Kraft pulp as described in Example 2, dry basis.

EXAMPLE 3

A layered paper sheet is produced in accordance with the process illustrated and described in connection with FIG. 1. Additional details of the papermaking machinery are as in Example 2, unless otherwise specifically noted.

Fibrous pulp type A is the product of Example 1. Fibrous pulp type B is a mixture of chemithermomechanical pulp (Quesnel Co.) and bleached northern softwood kraft pulp (Grand Prairie, P&G Cellulose). The type A pulp is made up into a stock having a consistency of about 0.6% in chest 1 using water having a hardness of less than 5 ppm (calcium plus magnesium). Process water supplies used at other stages of the papermaking operation have hardness of about 100 ppm (calcium plus magnesium). No cationic materials, whether in the form of cationic wet-strength resins or aqueous polyvalent metal cations, are added at any stage. Aqueous concentrated sulfuric acid is in storage vessel 3. The aqueous dispersion of type A pulp in chest 1 has a pH of about 3.5. The pH of the aqueous dispersion of type B pulp in chest 2 is about 3.5 and the consistency is about 3%. The headbox 12 is a Fixed Roof Former, equipped with (a) a multi-orifice distribution plate to redirect incoming furnish and distribute it equally over the width of the first foraminous member, (b) a chamber to promote turbulence in the distributed flow and to prevent flocking, (c) a flow channel to carry the furnish to the first foraminous member and (d) distribution leaves to further promote turbulence.

As distinct from Example 2, where a single stream of diluted pulp passes from the fan pump to the headbox, in the instant example, the distribution leaves of the headbox are now arranged to deliver type A and type B pulps as three separate streams, so in the web as laid down, there are two outer layers comprised of type B pulp, and the type A pulp is in the middle layer, i.e., is "sandwiched" between layers of type B pulp. In order to keep the type A and type B pulps separate prior to web lay-down, the fan-pump configuration 11 has three parallel pumps, rather than a single pump, and the type A and type B pulps do not contact each other, even when they are diluted by the recirculating process water flowing through the fan pumps. The consistency of each of the three streams of acidic stock at the headbox is about 0.15–0.20%. First foraminous member 15 is a fine-mesh Fourdrinier wire, as described in Example 2. A layered embryonic web is laid down, a type B pulp layer being laid down on the wire side, that is to say, adjacent to the Fourdrinier wire. The single stream of type A pulp is codeposited from the headbox as a second layer of pulp, superposed on the wire-side layer of type B pulp. A third layer (the composition of which is exclusively type B pulp) is codeposited from the headbox, superposed on the type A pulp layer. The pH of water draining from this three-layer embryonic web is about 3.5. The embryonic web travels as shown in FIG. 1 until it is transferred to second foraminous member 21 with the assistance of a vacuum pickup shoe, operating as described in Example 2. Second foraminous member 21 is a woven transfer fabric of open-mesh construction as described in Example 2.

The paper web arrives at alternate spray point 29a and is there treated with aqueous potassium carbonate having a concentration of about 4M (moles per liter) by means of a VIB sprayer as described in Example 2. The web now has a consistency of about 21% and enters a forced air predryer 28 of the same type as described in connection with Example 1. The predryer inlet temperature is about 170° C. On leaving the predryer, the paper web has a consistency of about 50%. The web continues motion indicated by motion arrow 26, and arrives at a conventional Yankee dryer arrangement 33, whereon the paper web is finally dried. The Yankee dryer includes conventional adhesive applicator means and a doctor blade for creping. The Yankee temperature, glue application and creping are all as in Example 2. The properties of the resulting paper sheet are set forth below:

| | |
|---|---|
| Process pH prior to alkali treatment | 3.5 |
| pH of paper | 7.7 |
| Pulp composition (% as laid down) | |
| Type A | 15.0 |
| Type B CTMP | 25.0 |
| NSK | 60.0 |
| Creped Basis Weight | |
| (lb/3000 sq. ft) | 16.9 |
| (g/sq. meter) | 27.6 |
| Absorbency of type A pulp (TBGV, g/g, pH 7-8) | 37.0 |
| Absorbency of paper (TBGV, g/g) | 8.5 |
| Absorbency Rate of paper (sec) | less than 10.0 |
| Spill Wipe Up, measured as two plies | significantly better than either of two controls (Example 7 and commercial BOUNTY towels) |
| Integrity of type A pulp in paper (VELM) | good |
| Caliper under load of 95 g/ 5 cm dia. | |
| (mils) | 12.4 |
| (millimeter) | 0.314 |
| Density (g/cm$^3$) | 0.087 |
| Dry Tensile Strain (%) | |

| | |
|---|---|
| Machine Direction | 23.3 |
| Cross Machine Direction | 4.8 |
| Dry Tensile Force: 4 inch (10.16 cm) gauge length | |
| Machine Direction (g/in) | 442 |
| (g/cm) | 174 |
| Cross Machine Direction (g/in) | 395 |
| (g/cm) | 155 |
| Wet Tensile Force: 4 inch (10.16 cm) gauge length | |
| Machine Direction (g/in) | 11 |
| (g/cm) | 4.3 |
| Cross Machine Direction (g/in) | 9 |
| (g/cm) | 3.5 |

EXAMPLE 4

A paper sheet is produced in accordance with the process illustrated and described in connection with FIG. 1. The materials and process are as in Example 2, with the exception that the proportion of chemithermomechanical pulp is reduced 5% and the proportion of type A pulp (material from Example 1) is increased 5%. The properties of the resulting paper sheet are set forth below:

| | |
|---|---|
| Process pH prior to alkali treatment | 3.5 |
| pH of paper | 8.0 |
| Pulp composition (% as laid down) | |
| Type A | 20.0 |
| Type B CTMP | 20.0 |
| NSK | 60.0 |
| Creped Basis Weight | |
| (lb/3000 sq. ft) | 17.0 |
| (g/sq. meter) | 27.7 |
| Absorbency of type A pulp (TBGV, g/g) | 37.0 |
| Absorbency of paper (TBGV, g/g) | 9.8 |
| Absorbency Rate of paper (sec) | less than 10.0 |
| Spill Wipe Up, measured as two plies | significantly better than two controls (Example 7 and commercial BOUNTY towels) |
| Integrity of type A pulp in paper (VELM) | good |
| Caliper under load of 95 g/5 cm dia. | |
| (mils) | 12.5 |
| (millimeter) | 0.316 |
| Density (g/cm³) | 0.089 |
| Dry Tensile Strain (%) | |
| Machine Direction | 19.0 |
| Cross Machine Direction | 3.2 |
| Dry Tensile Force: 4 inch (10.16 cm) gauge length | |
| Machine Direction (g/in) | 698 |
| (g/cm) | 275 |
| Cross Machine Direction (g/in) | 651 |
| (g/cm) | 256 |
| Wet Tensile Force: 4 inch (10.16 cm) gauge length | |
| Machine Direction (g/in) | 16 |
| (g/cm) | 6.3 |
| Cross Machine Direction (g/in) | 14 |
| (g/cm) | 5.5 |

EXAMPLE 5

A paper sheet is produced in accordance with the process illustrated and described in connection with FIG. 1, with the important exception that no alkali spray-on operation is carried out; i.e., as compared with Example 2, no potassium carbonate is sprayed onto the web. Accordingly, the Example 5 process is not a preferred embodiment of the invention. The properties of the resulting paper sheet, are set forth below:

| | |
|---|---|
| Process pH | 3.5 |
| pH of paper | 4.2 |
| Pulp composition (% as laid down) | |
| Type A | 15.0 |
| Type B CTMP | 25.0 |
| NSK | 60.0 |
| Creped Basis Weight | |
| (lb/3000 sq. ft) | 14.3 |
| (g/sq. meter) | 23.3 |
| Absorbency of type A pulp (TBGV, g/g, pH 7-8) | 37.0 |
| Absorbency of paper (TBGV, g/g) | 2.7 |
| Absorbency Rate of paper (sec) | less than 10.0 |
| Caliper under load of 95 g/5 cm dia. | |
| (mils) | 11.4 |
| (millimeter) | 0.29 |
| Density (g/cm³) | 0.081 |
| Dry Tensile Strain (%) | |
| Machine Direction | 19.5 |
| Cross Machine Direction | 3.7 |
| Dry Tensile Force: 4 inch (10.16 cm) gauge length | |
| Machine Direction (g/in) | 552 |
| (g/cm) | 217 |
| Cross Machine Direction (g/in) | 465 |
| (g/cm) | 183 |
| Wet Tensile Force: 4 inch (10.16 cm) gauge length | |
| Machine Direction (g/in) | 40 |
| (g/cm) | 15.8 |
| Cross Machine (g/in) | 32 |
| (g/cm) | 12.6 |

COMPARATIVE EXAMPLES 6, 7 AND 8

Paper sheets are produced, not in accordance with the process of the invention in the following specific respects:

Example 6: no alkali treatment is used and no type A pulp is used. The web consistency immediately prior to entering the pre-dryer is about 25.0%

Example 7: no type A pulp is used and wet-laying is carried out at a pH of 8 and no acid is added at any stage in the process.

Example 8: wet-laying is carried out at a pH of 8 and no acid is added at any stage in the process. The web consistency immediately prior to entering the pre-dryer is about 16.3%.

The properties of the resulting paper sheets are set forth below:

| Paper Properties for Comparative Example 6 | |
|---|---|
| Process pH | 3.5 |
| pH of paper | 4.0 |
| Pulp composition (% as laid down) | |
| Type A | 0 |
| Type B CTMP | 40.0 |
| NSK | 60.0 |
| Creped Basis Weight | |
| (lb/3000 sq. ft) | 14.3 |
| (g/sq. meter) | 23.3 |
| Absorbency of type A pulp (TBGV, g/g) | not present |
| Absorbency of paper (TBGV, g/g) | 2.8 |
| Caliper under load of 95 g/5 cm dia. | |
| (mils) | 12.0 |
| (millimeter) | 0.30 |
| Density (g/cm³) | 0.077 |
| Dry Tensile Strain (%) | |
| Machine Direction | 18.6 |
| Cross Machine Direction | 3.2 |
| Dry Tensile Force: 4 inch (10.16 cm) gauge length | |
| Machine Direction (g/in) | 329 |
| (g/cm) | 129 |

| -continued | |
| --- | --- |
| Cross Machine Direction (g/in) | 238 |
| (g/cm) | 94 |
| Wet Tensile Force: 4 inch (10.16 cm) gauge length | |
| Machine Direction (g/in) | 20 |
| (g/cm) | 7.9 |
| Cross Machine Direction (g/in) | 18 |
| (g/cm) | 7.1 |
| Paper Properties for Comparative Example 7 | |
| Process pH | 8.0 |
| pH of paper | 8.0 |
| Pulp composition (% as laid down) | |
| Type A | 0 |
| Type B CTMP | 40.0 |
| NSK | 60.0 |
| Creped Basis Weight | |
| (lb/3000 sq. ft) | 14.1 |
| (g/sq. meter) | 23.0 |
| Absorbency of type A pulp (TBGV, g/g) | not present |
| Absorbency of paper (TBGV, g/g) | 2.6 |
| Caliper under load of 95 g/5 cm dia. | |
| (mils) | 12.6 |
| (millimeter) | 0.32 |
| Density (g/cm$^3$) | 0.076 |
| Dry Tensile Strain (%) | |
| Machine Direction | 17.1 |
| Cross Machine Direction | 3.8 |
| Dry Tensile Force: 4 inch (10.16 cm) gauge length | |
| Machine Direction (g/in) | 350 |
| (g/cm) | 138 |
| Cross Machine Direction (g/in) | 295 |
| (g/cm) | 116 |
| Wet Tensile Force: 4 inch (10.16 cm) gauge length | |
| Machine Direction (g/in) | 8 |
| (g/cm) | 3.1 |
| Cross Machine Direction (g/in) | 6 |
| (g/cm) | 2.4 |
| Paper Properties for Comparative Example 8 | |
| Process pH | 8.0 |
| pH of paper | 8.0 |
| Pulp composition (% as laid down) | |
| Type A | 10.0 |
| Type B CTMP | 30.0 |
| NSK | 60.0 |
| Creped Basis Weight | |
| (lb/3000 sq. ft) | 14.0 |
| (g/sq. meter) | 22.8 |
| Absorbency of type A pulp (TBGV, g/g) | 37.0 |
| Absorbency of paper (TBGV, g/g) | 3.6 |
| Integrity of type A pulp in paper (VELM) | degraded |
| Caliper under load of 95 g/5 cm dia. | |
| (mils) | 10.5 |
| (millimeter) | 0.27 |
| Density (g/cm$^3$) | 0.085 |
| Dry Tensile Strain (%) | |
| Machine Direction | 17.2 |
| Cross Machine Direction | 4.1 |
| Dry Tensile Force: 4 inch (10.16 cm) gauge length | |
| Machine Direction (g/in) | 742 |
| (g/cm) | 292 |
| Cross Machine Direction (g/in) | 580 |
| (g/cm) | 228 |
| Wet Tensile Force (g/in) 4 in gauge length | |
| Machine Direction (g/in) | 39.5 |
| (g/cm) | 15.5 |
| Cross Machine Direction (g/in) | 11.1 |
| (g/cm) | 4.4 |

EXAMPLE 9

A paper sheet is produced in accordance with the process illustrated and described in connection with FIG. 1. Conditions are closely similar to Example 2, with the important exception that 1% glyoxylated anionic polyacrylamide, made in accordance with Example 6 of hereinbefore referenced U.S. Pat. No. 3,556,932, is used as a wet-strength additive. This additive, mixed with water, is uniformly sprayed as a mist or aerosol onto the paper web across its full width at any convenient position on the paper machine which is situated following the alkali-spraying stage of the process (29 or 29a) yet prior to the Yankee dryer (33). The properties of the resulting paper sheet are set forth below:

| | |
| --- | --- |
| Process pH prior to alkali treatment | 3.5 |
| pH of paper | 7.6 |
| Pulp composition (% as laid down) | |
| Type A | 15.0 |
| Type B CTMP | 25.0 |
| NSK | 60.0 |
| Creped Basis Weight | |
| (lb/3000 sq. ft) | 16.4 |
| (g/sq. meter) | 26.7 |
| Absorbency of type A pulp (TBGV, g/g at pH 7-8) | 38.0 |
| Absorbency of paper (TBGV, g/g) | 8.0 |
| Absorbency Rate of paper (sec) | less than 10.0 |
| Spill Wipe Up, measured as two plies | significantly better than control (Example 7) or commercial BOUNTY towel |
| Integrity of type A pulp in paper (VELM) | good |
| Caliper under load of 95 g/5 cm dia. | |
| (mils) | 10.8 |
| (millimeter) | 0.27 |
| Density (g/cm$^3$) | 0.097 |
| Dry Tensile Strain (%) | |
| Machine Direction | 19.3 |
| Cross Machine Direction | 5.1 |
| Dry Tensile Force: 4 inch (10.16 cm) gauge length | |
| Machine Direction (g/in) | 680 |
| (g/cm) | 267 |
| Cross Machine Direction (g/in) | 531 |
| (g/cm) | 209 |
| Wet Tensile Force: 4 in gauge length | |
| Machine Direction (g/in) | 102 |
| (g/cm) | 40.1 |
| Cross Machine Direction (g/in) | 71.5 |
| (g/cm) | 28.1 |

Test Methods

The following characterizing methods are useful in connection with the process and product of the invention: these methods are also used for making the measurements which are reported in the Examples hereinabove:

Creped Basis Weight (lb/3000 sq. ft): determined according to TAPPI method T410-OM-83. Basis weight in metric units is computed from the basis weight (lb/3000 sq. ft), multiplying by a factor of approximately 1.63.

Absorbency of type A pulp (TBGV, g/g) as well as Absorbency of paper (TBGV, g/g): The following is a gravimetric method (the Tea Bag Gel Volume or TBGV method) suitable for determining the equilibrium water absorbency of fibrous pulp type A, fibrous pulp type B, or paper webs derived therefrom:

Equipment is as follows:

Sample holders: glass cylinders open at both ends, 1.4 cm inside diameter, 3.4 cm height.

Tea-bag material: Tea-bag paper, grade 1234T, obtainable from the C. H Dexter Division of the Dexter Corp., Windsor Locks, Conn. This paper is cut into 4.0×7.2 cm rectangles. The purpose of the tea-bag material is to provide a substantially non-absorbent pulp-retaining material through which water will pass during centrifugation, and which acts to prevent the possibility of obtaining artificially high pulp absorbencies, which might otherwise occur, e.g., if the pulp were allowed to block the constriction in the centrifuge tube.

Balance: 0.0001 g sensitivity.

Centrifuge: clinical model, variable speed, with a swinging bucket rotor, four 29.4 mm inside diameter ×95 mm depth shields, and tachometer adapted to measure centrifuge speed.

Centrifuge tubes: designed with a constriction so that on centrifuging, the water will separate into the lower half of the tube, leaving the sample and "tea-bag" in the upper half.

Drying beakers: 10 ml capacity.

Vacuum oven: capable of approximately 250 mTorr vacuum, heating to at least 110° C.; temperature thermostatted at 60° C.

Convection oven: thermostatted at 105° C.

Soaking beakers: 25–30 ml capacity.

For each absorbency determination, a number of replicated measurements (typically 5) are made, each based on the following procedure: Weigh a 4.0×7.2 cm rectangular tea-bag paper. The weight is the Initial Teabag Weight (Initial Teabag Weight=ITB) and is typically of the order of 50 mg. Fold and place it inside a sample holder so as to form a container or "tea-bag" for the paper or pulp sample. Place a sample of fibrous pulp or paper web (wet or dry) in the "tea-bag". (Typically the sample is sufficient to contain about 100 mg bone dry pulp.) Place the combined sample, "tea-bag" and sample holder in a soaking beaker. Fill the soaking beaker with distilled water (pH 7–8), to a height corresponding with the top edge of the sample holder. Allow to equilibrate overnight. Place sample and "tea-bag" in a centrifuge tube. Centrifuge at approximately 125 g (gravities) force for 10 minutes, centrifuge speed-up time not included. Place the centrifuged sample and "tea-bag" in an accurately preweighed dry beaker (dry beaker weight=DBW). Weigh the centrifuged sample, teabag and beaker (weight=$W_1$). Dry in the 105° C. convection oven for 3 hours. Further dry in the vacuum oven for 6 hours or more. Allow to cool in a desiccator. Weigh (weight=$W_2$). The absorbency of the sample (TBGV, g/g) is given by the following formula:

$$TBGV = (WPW - DPW)/DPW$$

wherein WPW = wet pulp weight = $W_1 - (ITB + DBW)$ and DPW = dry pulp weight = $W_2 - (ITB + DBW)$.

In principle, it is possible to measure TBGV absorbency at pH values other than those in the range 7–8 of the above-specified method. However, unless there is a specific mention of another pH, any TBGV absorbency value quoted throughout the instant specification and claims, expressed simply in g/g, is strictly to be construed as a measurement at a pH in the range 7–8.

Absorbency Rate of paper (sec) (This method is identified elsewhere in the specification as "VELM method". "VELM" is an acronym for "Video Enhanced Light Microscopy" since in practice, it is convenient, albeit not essential, to attach a television camera to the light microscope and to observe the pulp fibers swelling by means of a television screen). The essential aspects of the method are as follows: Absorbency rate is determined on the basis of the time required for type A pulp fibers to reach 90% of their maximum swelling. Whether making the determination on loose fibers or on the type A pulp fibers within a paper sheet, the procedure involves microscopic examination, as follows: Place a sample of type A pulp, or paper containing type A pulp, in the field of a light microscope. Apply a dilute aqueous solution of Toluidine Blue (0.01–0.1%), timing swelling of the fibers as of the time at which they are contacted by the solution. The type A pulp fibers are selectively stained by the cationic dye, and swell rapidly. Thus, stained Type A pulp is pink. For comparison, stained chemithermomechanical pulp is dark blue and stained kraft pulp is light blue. Observation is continued for 10 minutes, at which time the type A pulp fibers are generally fully swollen. The type A pulp starting material is of good quality for the purposes of the instant invention when fibers thereof swell to 90% or more of their full (10 minute) capacity within 10 seconds or less. When paper is produced in accordance with the preferred process of the invention (having both acid treatment and alkali treatment steps), then the type A pulp in the paper retains its integrity and swells to 90% or more of the full (10 minute) capacity within 10 seconds or less.

Spill Wipe Up, measured as two plies: Single-ply paper according to the process of the invention is conventionally converted to two-ply paper, without using glue or gluing the plies very lightly. Spill wipe-up capability of the two-ply paper is evaluated by a group of 48 panelists who, without being told which is the test paper and which is the control paper, are asked to wipe up aliquots of 5, 10 and 20 ml of water from a table surface using the paper samples. As control paper, the panelists are provided with conventional two-ply towels made from the conventional paper of Example 7 or commercially obtained BOUNTY towels. The panelists complete forms indicating spill wipe-up preferences.

Integrity of type A pulp in paper

Integrity of type A pulp in paper is qualitatively determined by light microscopy. An experienced operator qualitatively judges whether degradation has occurred, using as guideline the proportion of Toluidine Blue-stained intact type A fibers in relation to Toluidine Blue-stained non-fibrous material (fines, appreciably fibrillated fiber fragments).

Caliper (mils, i.e., thousandths of an inch) under load of 95 g/ 5 cm dia.: Caliper of paper is measured by TAPPI Standard Method T411-OM-84, using a VIR Electronic Thickness Tester, Model 89-II-F. Caliper (millimeters) is computed using the factor I inch=25.4 millimeters.

Density: The density of a paper web can be obtained by dividing the Basis Weight by the thickness, that is to say, the Caliper. The Basis Weight and Caliper are directly measured, as noted supra. The formula is:

Density (grams per cubic centimeter) = Basis Weight (pounds per 3000 square feet) / Caliper (thousandths of an inch) ×8.602.

Dry Tensile Strain, Dry Tensile Force and Wet Tensile Force: These are measured using TAPPI Standard Methods T456-OM-82 and T494-OM-81 at the standard conditioning and testing atmosphere described in TAPPI T402-OM-83 with the following modification:

A. The rate of jaw separation is 0.5 in/min (1.27 cm/min).

B. Both clamp jaws are flat.

C. Calculation is by computer rather than manual.

pH of papermaking process water herein does not have to be determined by on-line pH sensing means and can equally well be directly measured using conventional equipment. pH values of test water in equilibrium with test samples of pulp or paper, less formally termed "pH of pulp" or "pH of paper", can conveniently be measured as follows. A sample of pulp or paper from the papermaking process of the invention is placed in a suitably sized wide-mouthed jar which has a removable cap. The size of the sample should be such as to contain from two to four grams of pulp or paper, bone dry basis. Deionized water is added to the sample, so that the total volume is in the range 150–200 milliliters. The jar is then capped and the sample is shaken for about 1 minute, after which 1. 5 milliliters of ORION pHIX (TM) brand pH adjustor solution, Orion Catalog number 700003, or equivalent, is added. The jar is once again capped and is shaken vigorously for 15 seconds. A pH meter equipped with an Orion Ross combination pH electrode, calibrated using at least two standard buffer solutions, preferably at pH 4 and pH 10, is used to test the pH of the test water in the jar.

Additional notes in relation to defining pH, acidification and alkali treatment:

Unless there is contrary or more specific notation, "pH" as referred to herein will be taken as relating to pH of water (e.g., process water or aqueous pulp-dispersing medium) which is at equilibrium with a fibrous pulp at least to the extent that a pH measurement meaningful to one of ordinary skill can be taken. Unless there is contrary or more specific notation, "acidification" as a step in the process of the invention will be taken as referring to addition of sufficient acid to significantly decrease pH, arriving at an absolute pH value below 7, more preferably more than two pH units below 7. Unless there is contrary or more specific notation, "alkali-treatment" or "addition of alkali" refers to addition of sufficient alkali to significantly increase pH. These terms use a different convention as compared with "acidification". While "acidification" is defined as reaching absolute pH below 7, alkali treatment or addition of alkali do not invariably require arriving at an absolute pH above 7; for most practical purposes herein, reaching a pH of about 6 or higher apon alkali treatment is considered sufficient alkali treatment. Very preferably, alkali treatment results in pH values of about 7.5 to about 9.

What is claimed is:

1. In a continuous wet-laying papermaking process for the manufacture of absorbent paper sheets from two or more fibrous cellulosic pulps, wherein at least one of said fibrous cellulosic pulps, A, is a polymer-modified fibrous cellulosic pulp, capable of being protonated, which, in its alkali-metal-cation exchanged state, imbibes water by hydrocolloidal swelling, and wherein the balance of said fibrous cellulosic pulps, B, is non-polymer modified and comprises conventional cellulosic papermaking pulps, said process comprising the steps of web lay-down and dewatering starting from an aqueous suspension, slurry or stock containing a mixture of the pulps, the improvement which comprises conducting the wet-laying process by wet-laying an acidified mixture of the A and B pulps in the absence of interfering cationic materials, under conditions wherein pulp A is laid down in an embryonic web in the protonated state and wherein said embryonic web is at least partially dewatered while maintaining pulp A in said protonated state; said process comprising the sequence of steps:

(a) treating stock of said fibrous cellulosic pulps with acid; the amount of said acid being sufficient to ensure that in subsequent step (b), the type A component of said fibrous pulps is maintained in said protonated state;
   (b) wet-laying the acidic stock formed in step (a) from a single-channel or multi-channel headbox onto a first foraminous member, thereby draining water to the extent of forming an embryonic web, said embryonic web having one or more layers;
   (c) at least partially dewatering the embryonic web in one or more steps to provide a partially dewatered web;
   (d) contacting the partially dewatered web of step (c) with an aqueous solution of alkali so as to at least partially bring the fibrous cellulosic pulp type A component of the web to the alkali-metal cation-exchanged state; and
   (e) drying the web.

2. The process of claim 1, wherein fibrous pulp type A is further characterized in that it comprises a covalently chemically bonded polymeric modifier consisting essentially of a hydrophilic organic polycarboxylate polymer, and wherein the web temperature throughout steps (a)-(e) has an upper limit of about 200° C.

3. The process of claim 2, wherein the amount of acid is such as to deliver a pH in the range from about 3 to about 5, as determined in the water draining from said embryonic web.

4. The process of claim 3, wherein immediately prior to step (d), said partially dewatered web has a consistency in the range from about 15% to about 75%.

5. The process of claim 4, wherein said fibrous pulps consist essentially of: from about 1% to about 20% of fibrous pulp type A and from about 80% to about 99% of fibrous pulp type B, dry basis; and wherein said fibrous pulp type B is selected from the group consisting of kraft pulp, sulfite pulp and chemithermomechanical pulp; said acid is sulfuric acid; said alkali is selected from the group consisting of sodium hydroxide, sodium bicarbonate, sodium carbonate, potassium hydroxide, potassium bicarbonate and potassium carbonate; and wherein the alkali-contacting means in step (d) are comprised of a conventional spray-head.

6. The process of claim 5, wherein step (e) is carried out using a conventional Yankee dryer, the drum temperature of which is in the range from about 150° C. to about 175° C.

7. The process of claim 2, wherein the pH of water draining from the web in each of steps (b) and (c) is in the range from about 3.5 to about 4.5 and wherein the pH of a water sample, extractable by sqeezing a sample of the web, at the end of step (d) is in the range from about 6 to about 9.

8. The process of claim 7 wherein partial web-dewatering is accomplished by the sequence of steps, in (c), of:

(c-i) mechanically dewatering said embryonic web on said first foraminous member using conventional means;
   (c-ii) transferring said embryonic web to a second foraminous member consisting of an open-weave imprinting fabric or deflection member and further mechanically dewatering the web thereon to a consistency in the range from about 15% to about 25%; and (c-iii) thermally predrying using conventional means, thereby arriving at said partially dewatered web.

9. The process of claim 8 wherein said conventional means in step (c-iii) consist of a conventional forced air predryer, the air inlet temperature of which is maintained in the range from about 125° C. to about 175° C.

10. The process of claim 9 wherein additional wet-strength is imparted to the web by an additional, wet-strength-adding step, comprising spray-on to the web, by means of a conventional spray-head, of a wet-strength additive selected from the group consisting of glyoxylated anionic polyacrylamides; said additional, wet-strength-adding step intervening at any stage of said process between step (b) and step (e).

11. The process of claim 10, wherein said additional, wet-strength-adding step is positioned immediately after step (d) and immediately prior to step (e).

12. The process of claim 9, wherein said polymer-modified fibrous pulp type A as used in step (a) is the product of a grafting-and-hydrolysis process comprising: starting from a substrate pulp selected from the group consisting of kraft pulp and sulfite pulp, grafting said substrate pulp by reaction thereof in the presence of a polymerization initiator with one or more compatible monomers and hydrolyzing under mild conditions the intermediate fibrous graft copolymer so formed, thereby providing said polymer-modified pulp type A having said organic polycarboxylate polymer formed in-situ covalently chemically bonded in or upon said substrate pulp.

13. The process of claim 12, wherein said grafting-and-hydrolysis process for preparing said polymer-modified pulp type A is further characterized in that it comprises grafting substrate pulp selected from softwood kraft pulp, in an aqueous medium in the presence of the polymerization initiator selected from the group consisting of a water-soluble salt of Ce(IV), Fe(II) or Mn(III) with one or more of the compatible monomers selected from the group consisting of methyl acrylate, ethyl acrylate, acrylonitrile, acrylamide and mixtures thereof.

14. The process of claim 13, wherein said grafting-and-hydrolysis process for preparing said polymer-modified pulp type A is further characterized in that said polymerization initiator is ceric ammonium nitrate, said compatible monomer is methyl acrylate, said substrate pulp is at a level of from about 20% to about 50%, said polymerization initiator is at a level of from about 0.5% to about 3% and said compatible monomer is at a level of from about 50% to about 80%.

15. The process of claim 14, wherein said grafting-and-hydrolysis process for preparing said polymer-modified pulp type A is further characterized in that said polymerization initiator is the last-added component.

16. The process of claim 15, wherein said grafting-and-hydrolysis process for preparing said polymer-modified pulp type A is further characterized in that said substrate pulp, polymerization initiator and compatible monomer are reacted together in said aqueous medium at low shear under an inert atmosphere at a temperature from about 10° C. to about 40° C. for a period of from about 0.5 hours to about 10 hours.

17. The process of claim 16 wherein the intermediate fibrous graft copolymer is filtered and substantially fully hydrolyzed to remove hydrophobic groups present in said compatible monomer, by reaction with water and sodium hydroxide, the initial aqueous concentration of said intermediate fibrous graft copolymer being in the range from about 0.5% to about 10% and the initial aqueous sodium hydroxide concentration being in the range from about 1% to about 5%; with a hydrolysis temperature in the range from about 80° C. to about 100° C., a hydrolysis time period in the range from about 0.5 hours to about 2 hours and an approximately atmospheric hydrolysis pressure.

18. The process of claim 17, wherein polymer-modified pulp type A is filtered as the product at the end of said hydrolysis step and is used in step (a) of said papermaking process without any intervening step of grinding, extruding, sonicating, or beating.

19. The process of claim 18, wherein polymer-modified pulp type A is filtered at the end of said hydrolysis step and is used in step (a) of said papermaking process without any intervening step of thermally drying.

20. An absorbent structure, in the form of wet-laid paper sheet, comprising: from about 5% to about 15% of fibrous pulp type A, consisting essentially of a polymer-modified fibrous pulp having distinct protonated and alkali-metal-cation-exchanged states; which pulp, as characterized in the protonated state, has relatively non-swollen fibrous morphology and which, as characterized in the alkali-metal-cation-exchanged state, has the form of a substantially fibrous polyanionic hydrocolloid further characterized by hydrocollodial swelling upon wetting, to the extent that said fibrous pulp type A has a water or aqueous fluid absorbency of from about 20g/g to about 60g/g, measured by the TBGV method, and a rate of water or aqueous fluid absorption such that said fibrous pulp type A reaches at least 90% of its maximum water-absorbing capacity within 10 seconds, measured by the VELM method; said polymer-modified fibrous pulp type A in the alkali-metal-cation-exchanged state being relatively fragile and difficult to dewater when wet as compared with conventional papermaking fibers and being susceptible to deactivation as an absorbent upon exposure to either of both of the classes of cationic materials (i) multivalent metal ions such as are commonly present in papermaking process water and (ii) cationic polymers or cationic polyelectrolytes conventionally known for use in papermaking for improving paper wet-strength; said polymer-modified fibrous pulp further being characterized by a significant relative decrease in fragility, increase in ease of dewatering and increase in resistance to multivalent metal ions in the protonated state as compared with said alkali-metal-cation-exchanged state;

the balance comprising conventional papermaking pulps and, non-interfering wet-strength additives, said additives being in the form of from 0.1% to 2% of a glyoxylated anionic polyacrylamide;

said paper sheet being characterized by a density in the range from about 0.05 g/cm$^3$ to about 0.25 g/cm$^3$; a mean water or aqueous fluid absorbency of the sheet in the range from about 2 g/g to about 10 g/g as measured by the TBGV method; and a total wet tensile, machine direction plus cross-machine directions, in the range from about 500 g/inch to about 1500 g/inch; said paper sheet being the product of a process comprising both wet-laying said pulps and at least partially dewatering the resulting wet paper sheet whilst maintaining fibrous pulp type A in the protonated state; said wet-laying and partial dewatering operations being conducted in the substantial absence of interfering cationic materials.

* * * * *

UNITED STATES PATENT AND TRADEMARK OFFICE
CERTIFICATE OF CORRECTION

PATENT NO.  : 4,986,882
DATED       : January 22, 1991
INVENTOR(S) : Larry N. Mackey and Seyed E. Seyed-Rezai It is certified that error appears in the above-identified patent and that said Letters Patent is hereby corrected as shown below:

Column 7, line 22, "q" should be deleted.

Column 15, line 13, --On-- should be inserted at beginning of sentence.

Column 18, line 49, "8°C" should be --80°C--.

Column 26, line 26, "1M' should be --31M--.

Signed and Sealed this

Third Day of November, 1992

Attest:

DOUGLAS B. COMER

Attesting Officer

Acting Commissioner of Patents and Trademarks